(12) United States Patent
St. Anne et al.

(10) Patent No.: US 9,492,260 B2
(45) Date of Patent: Nov. 15, 2016

(54) SYSTEMS AND METHODS FOR TREATING FEMALE INCONTINENCE AND PELVIC NERVE DYSFUNCTION

(71) Applicant: ParaPatch, Inc., Inglewood, CA (US)

(72) Inventors: Cora St. Anne, Inglewood, CA (US); Joseph St. Anne, Inglewood, CA (US); Cindy Santa Cruz, Inglewood, CA (US); Theodore V. Benderev, San Juan Capistrano, CA (US); Eric Willis, Santa Cruz, CA (US); Kevin Wasserstein, Menlo Park, CA (US)

(73) Assignee: ParaPatch, Inc., Campbell, CA (US)

( * ) Notice: Subject to any disclaimer, the term of this patent is extended or adjusted under 35 U.S.C. 154(b) by 0 days.

(21) Appl. No.: 14/770,446

(22) PCT Filed: Feb. 25, 2014

(86) PCT No.: PCT/US2014/018445
§ 371 (c)(1),
(2) Date: Aug. 25, 2015

(87) PCT Pub. No.: WO2014/134073
PCT Pub. Date: Sep. 4, 2014

(65) Prior Publication Data
US 2016/0022399 A1 Jan. 28, 2016

Related U.S. Application Data

(63) Continuation-in-part of application No. 13/776,930, filed on Feb. 26, 2013, now Pat. No. 9,408,683.

(51) Int. Cl.
*A61F 2/00* (2006.01)
*A61N 1/36* (2006.01)
(Continued)

(52) U.S. Cl.
CPC ........... *A61F 2/0009* (2013.01); *A61F 2/0022* (2013.01); *A61H 19/34* (2013.01);
(Continued)

(58) Field of Classification Search
CPC ...... A61F 2/0054; A61F 5/48; A61F 2/0009; A61F 2/0022; A61F 2/0013; A61F 6/04; A61F 5/41; A61F 6/24; A61F 6/22; A61F 6/20; A61F 2006/047; A61F 2006/048; A61F 5/453; A61F 13/471; A61F 5/4401; A61B 17/11
See application file for complete search history.

(56) References Cited

U.S. PATENT DOCUMENTS 3,646,616 A 3/1972 Keshin
3,762,415 A 10/1973 Morrison
(Continued)

FOREIGN PATENT DOCUMENTS

EP 0931530 A1 7/1999
WO WO 97/41818 A1 11/1997

OTHER PUBLICATIONS

"Incontinence—Urinary Leakage—A Common and Treatable Condition" Pamphlet, Kaiser Permanente (1995) in 11 pages.
(Continued)

*Primary Examiner* — Ophelia A Hawthorne
(74) *Attorney, Agent, or Firm* — Knobbe, Martens, Olson & Bear, LLP

(57) ABSTRACT

Systems and methods for neuromodulation of a female patient suffering from a pelvic condition, such as incontinence, are disclosed. A mechanical stimulus such as pressure, tension, traction, friction, or vibration for example can be applied to one, two, or more clitoral structures sufficient to cause a physiologic stimulus or inhibition, such as neuromodulation to treat or prevent the pelvic condition.

20 Claims, 8 Drawing Sheets

(51) Int. Cl.
*A61H 19/00* (2006.01)
*A61F 13/15* (2006.01)

(52) U.S. Cl.
CPC ....... *A61N1/36007* (2013.01); *A61N 1/36014* (2013.01); *A61F 2013/15121* (2013.01); *A61F 2210/0014* (2013.01); *A61F 2250/0036* (2013.01); *A61F 2250/0078* (2013.01); *A61H 19/50* (2013.01); *A61H 2201/165* (2013.01); *A61H 2201/1688* (2013.01)

(56) References Cited

U.S. PATENT DOCUMENTS

| | | |
|---|---|---|
| 3,789,828 A | 2/1974 | Schulte |
| 3,905,372 A | 9/1975 | Denkinger |
| 3,911,173 A | 10/1975 | Sprague, Jr. |
| 3,929,135 A | 12/1975 | Thompson |
| 4,191,609 A | 3/1980 | Trokhan |
| 4,202,925 A | 5/1980 | Dabroski |
| 4,324,246 A | 4/1982 | Mullane et al. |
| 4,342,314 A | 8/1982 | Radel et al. |
| 4,367,732 A | 1/1983 | Poulsen et al. |
| 4,463,045 A | 7/1984 | Ahr et al. |
| 4,486,193 A | 12/1984 | Shaw et al. |
| 4,573,986 A | 3/1986 | Minetola et al. |
| 4,610,678 A | 9/1986 | Weisman et al. |
| 4,782,535 A | 11/1988 | Yewer, Jr. et al. |
| 4,785,996 A | 11/1988 | Ziecker et al. |
| 4,822,347 A | 4/1989 | MacDougall |
| 4,834,735 A | 5/1989 | Alemany et al. |
| 4,842,666 A | 6/1989 | Werenicz |
| 4,846,819 A | 7/1989 | Welch |
| 4,850,986 A | 7/1989 | Temple |
| 4,875,898 A | 10/1989 | Eakin |
| 4,892,535 A | 1/1990 | Bjornberg et al. |
| 4,917,697 A | 4/1990 | Osborn, III et al. |
| 4,920,986 A | 5/1990 | Biswas |
| 4,944,734 A | 7/1990 | Wallach |
| 4,950,264 A | 8/1990 | Osborn, III |
| 5,006,394 A | 4/1991 | Baird |
| 5,007,894 A | 4/1991 | Enhorning |
| 5,074,855 A | 12/1991 | Rosenbluth et al. |
| 5,090,424 A | 2/1992 | Simon et al. |
| 5,131,906 A | 7/1992 | Chen |
| 5,263,947 A | 11/1993 | Kay |
| 5,308,887 A | 5/1994 | Ko et al. |
| 5,312,384 A | 5/1994 | Temple |
| 5,336,208 A | 8/1994 | Rosenbluth et al. |
| 5,383,867 A | 1/1995 | Klinger |
| 5,386,836 A | 2/1995 | Biswas |
| 5,417,226 A | 5/1995 | Juma |
| 5,509,427 A | 4/1996 | Simon et al. |
| 5,513,659 A | 5/1996 | Buuck et al. |
| 5,589,978 A | 12/1996 | Fantone |
| 5,669,395 A | 9/1997 | Thompson |
| 5,693,002 A | 12/1997 | Tucker et al. |
| 5,804,215 A | 9/1998 | Cubbage et al. |
| 5,843,011 A | 12/1998 | Lucas |
| 5,877,216 A | 3/1999 | Place et al. |
| 6,131,575 A | 10/2000 | Lenker et al. |
| 6,179,775 B1 | 1/2001 | Thompson |
| 6,224,541 B1 | 5/2001 | Thompson |
| 6,461,340 B1 | 10/2002 | Lenker et al. |
| 6,593,313 B2 | 7/2003 | Place et al. |
| 6,836,684 B1 | 12/2004 | Rijkhoff et al. |
| 6,949,067 B1 | 9/2005 | Dann et al. |
| 6,964,643 B2 | 11/2005 | Hovland et al. |
| 7,565,198 B2 | 7/2009 | Bennett et al. |
| 8,684,008 B2 | 4/2014 | St. Anne |
| 2002/0055761 A1 | 5/2002 | Mann et al. |
| 2002/0120219 A1 | 8/2002 | Hovland et al. |
| 2004/0242770 A1 | 12/2004 | Feldstein et al. |
| 2006/0239958 A1 | 10/2006 | Taguchi et al. |
| 2009/0118574 A1 | 5/2009 | Stephenson |
| 2010/0267302 A1 | 10/2010 | Kantner et al. |
| 2012/0160258 A1 | 6/2012 | Cruz et al. |
| 2012/0283615 A1 | 11/2012 | Malik et al. |
| 2013/0022734 A1 | 1/2013 | Murata et al. |
| 2013/0184778 A1 | 7/2013 | St.Anne et al. |
| 2014/0194550 A1 | 7/2014 | St. Anne |

OTHER PUBLICATIONS

"The selling of incontinence." Consumer Reports Oct. 1997 in 3 pages.

Document of record in the filed of parent U.S. Appl. No. 12/999,114 (now U.S. Pat. No. 8,684,008) filed on Nov. 14, 2013 entitled "Activities of inventor Cora St. Anne described in the accompanying Information Disclosure Statement Transmittal submitted herewith on Nov. 14, 2013 in 6 pages."

Akala et al. "Novel pH-sensitive hydrogels with adjustable swelling kinetics." Biomaterials, Jun. 1998, 19(11-12) 1037-47.

Baron J: Partial androgen insensitivity syndrome: Ginekologia Polska, Jun. 1994, 65(6):319-25. (Abstract only) in 1 page.

Baron, J.: Classical and Incomplete Androgen Insensitivity Syndromes; Ginekologia Polska, Jul. 1994, 65 (7):377-86. (Abstract only) in 1 page.

Benzl JS: Vaginal dysfunction; in Benson JT (ed): Female Pelvic Floor Disorders. Norton, 1992, Chapter 13, pp. 307-311 in 5 pages.

Bond, SJ; Seibel, N; Kapur, S; Newman, KD: Rhabdomyosarcoma of the clitoris; Cancer, Apr. 1, 1994, 73(7):1984-6. (Abstract only) in 1 page.

Chalker et al. Overcoming Bladder Disorders. Harper and Row (1990) pp. 3, 44, and 45 in 3 pages.

Chapter 11, "Sphincter Electromyography and Other Electrophysiological Tests" in Hald et al.: The Urinary Bladder, Neurology and Dynamics; Williams & Wilkins (1982), pp. 118-127 in 10 pages.

Chapter 12, "Uroflowmetry and Pressure-flow Investigations" in Hald et al.: The Urinary Bladder, Neurology and Dynamics; Williams & Wilkins (1982), pp. 128-140 in 13 pages.

Chapter 13, "Urethral Closure Pressure Profile," in Hald et al.: The Urinary Bladder, Neurology and Dynamics; Williams & Wilkins (1982), pp. 141-150 in 10 pages.

Chapter 16, "Urinary Incontinence," in Hald et al.: The Urinary Bladder, Neurology and Dynamics; Williams & Wilkins (1982), pp. 175-203 in 29 pages.

Chapter 22, "Pitfalls and Errors in Urodynamic Assessment," in Hald et al.: The Urinary Bladder, Neurology and Dynamics; Williams & Wilkins (1982), pp. 310-329 in 20 pages.

Chapters 1 and 2 in Hald et al.: The Urinary Bladder, Neurology and Dynamics; Williams & Wilkins (1982), pp. ix-21 in 22 pages.

Chapters 3 and 4, pp. 22-47 of "The Urinary Bladder—Neurology and Dynamics," Lippincott (1982) in 28 pages.

Colleselli K et al. The female urethral sphincter: a morphological and topographical study. J Urology, Jul. 1998, 160 (1): 49-54. (Abstract only) in 1 page.

Dahms et al. "The impact of sacral root anatomy on selective electrical stimulation for bladder evacuation." World J. Urology, 1998, 16(5):322-8 (Abstract only) in 1 page.

Dasgupta P; Haslam, C; Goodwin, R; Fowler, CJ; The 'Queen Square bladder stimulator': a device for assisting emptying of the neurogenic bladder: British Journal of Urology, Aug. 1997, 80(2):234-7. (Abstract only) in 1 page.

de Groat. Anatomy of the central neural pathways controlling the lower urinary tract. European Urology 1998, 34 Suppl. 1: 2-5 in 4 pages.

Deindl FM et al. "Dysfunctional voiding in women: which muscles are responsible?" British J. Urology, Dec. 1998, 82(6): 814-9 (Abstract only) in 1 page.

Deplanne et al. "The adrenergic, cholinergic, and NANC nerve-mediated contractions of the female rabbit bladder neck and proximal, medial and distal urethra." British J. Pharmacology, Apr. 1998 123(8):1517-24 (Abstract only) in 1 page.

DETROL product literature (1999) in 62 pages.

Di Benedetto, V; Di Benedetto, A; Introduction of the anterior sagittal trans-ano-rectal approach (ASTRA) as a technical variation

(56) References Cited

OTHER PUBLICATIONS of the Passerini-Glazel clitoro-vaginoplasty; preliminary results; Pediatria Medica E. Chirurgica, Jul.-Aug. 1997, 19(4):273-6. (Abstract only) in 1 page.
El Hemaly, AK; Mousa, LA; Stress urinary incontinence, a new concept; European Journal of Obstetrics, Gynecology, and Reproductive Biology, Sep. 1996, 68(1-2):129-35. (Abstract only) in 1 page.
Female Pelvic Floor Disorders—Investigation and Management (Benson, J.T., ed.), Norton Medical Books (1992); Chapter 11C3 by B.C. Eriksen, Electrical Stimulation, pp. 219-231 in 15 pages.
Feneley, Roger C. L., "Normal Micturition and Its Control" chapter in "Incontinence and its management," Croon Helm (1986) pp. 16-23 in 4 pages.
Fletcher, TF, Applied anatomy and physiology of the feline lower urinary tract. Veterinary Clinics of North America. Small Animal Practice, Mar. 1996, 26(2):181-96, Feb. 25, 1999 (Abstract only) in 1 page.
Fowler et al., Chapter 10, "Clinical Neurophysiology" in Torrens et al. "The Physiology of the Lower Urinary Tract," Springer-Verlag (1987) pp. 309-330 in 22 pages.
Franceschetti GP et al. Minimally invasive treatment of female urinary incontinence due to sphincter incompetence. Chirurgia Italiana, 1998, 50(1): 17-24. (Abstract only) in 1 page.
Frauscher et al. Intraurethral ultrasound: diagnostic evaluation of the striated urethral sphincter in incontinent females. Eur. Radiol. 8, 50-53 (1998) in 4 pages.
Gartley. Managing Incontinence. Jameson Books (1985) p. 15 in 1 page.
Glavind K. Use of a vaginal sponge during aerobic exercises in patients with stress urinary incontinence. Int'l Urogynecology Journal and Pelvic Floor Dysfunction 1997; 8(6): 351-3 (Abstract only) in 1 page.
Gosling JA. "Modification of bladder structure in response to outflow obstruction and ageing." Euro. Urology, 1997, 32 Suppl 1: 9-14 (Abstract only) in 1 page.
Hajivassiliou. The development and evolution of artificial urethral sphincters. J. Med. Engineering and Technology, Jul.-Aug. 1998, 22(4): 154-9 (Abstract only) in 1 page.
Hale DS et al., Histologic analysis of needle biopsy of urethral sphincter from women with normal and stress incontinence with comparison of electromyographic findings. Am. J. Obstet. And Gyn, 1999 Fed, 180: 342-8 in 7 pages.
Hollander et al.: Pelvic floor neuropathy; in Benson JT (ed): Female Pelvic Floor Disorders. Norton, 1992, Chapter 11, pp. 185-198 in 14 pages.
Huang et al. Preservation of pudendal afferents in sacral rhizotomies. Neurosurgery, Aug. 1997, 41(2):411-5 (Abstract only) in 1 page.
Incontinence: No Longer a Reason to Stay Home. Los Angeles Times Advertising Supplement Aug. 2, 1992 in 1 page.
INTROL Bladder Neck Support Prosthesis product literature. UroMed Corporation (1997) in 6 pages.
Jarvie et al. "Novel hydrophilic cyclic monomers in hydrogel synthesis." Biomaterials, Nov. 1998, 19 (21): 1957-61 (Abstract only) in 1 page.
Khullar V et al. The urethra (IPP, MUPP, instability, LPP). European Urology, 1998, 34 Suppl 1: 20-2. in 3 pages.
Kihara, K; de Groat, WC: Sympathetic efferent pathways projecting to the bladder neck and proximal urethra in the rat; Journal of the Autonomic Nervous System, Feb. 17, 1997, 62(3):134-42. (Abstract only) in 1 page.
Kouichi Ota, Tadao Yanagidani, Kazuhiro Kishikawa, Yuji Yamamori, and J.G. Collins: Cutaneous Responsiveness of Lumbar Spinal Dorsal Horn Neurons is Reduced by General Anesthesia, An Effect Dependent in Part on GABA-A Mechanisms; J Neurophysiol. 80: 1383-1390, (1998) in 14 pages.
Larosa et al. Valsalva leak point-pressure (LPP) and maximal urethral closure pressure (MUCP) in women with stress urinary incontinence (SUI). Archivio Italiano di Urologia, Andrologia Dec. 1997, 69(5):287-92 (Abstract only) in 1 page.
Li, P; Wilding, TJ; Kim, SJ; Calejesan, AA; Huettner, JE; Zhuo, M.:Kainate-receptor-mediated sensory synaptic transmission in mammalian spinal cord; Nature, Jan. 14, 1999, 397 (6715): 161-4. (Abstract only) in 1 page.
M. I. Resnick and A. C. Novick, "Urology Secrets" (1995) Chapter 42, pp. 133-138 in 6 pages.
McLennan et al. Supine empty stress test as a predictor of low valsalva leak point pressure. Neurourology and Urodynamics 1998, 17(2): 121-7 (Abstract only) in 1 page.
Meyer et al. Stimulated pressure profile at rest: a noninvasive method for assessing urethral sphincter function. Urology Oct. 1998, 52(4): 679-84 (Abstract only) in 1 page.
Morrison, Chapter 4, "Sensations arising from the lower urinary tract" in Torrens et al. "The Physiology of the Lower Urinary Tract," Springer-Verlag (1987) pp. 89-131 in 43 pages.
Nagamatsu et al. Evaluation of clinical indexes to predict fate of pelvic nerve dysfunction. Urol. Res. 1998, 26: 319-23 in 5 pages.
National Association for Continence—Literature (1997) in 6 pages.
O'Connell et al. Anatomical relationship between urethra and clitoris. J. Urology Jun. 1998, 159(6) 1892-7. (Abstract only) in 1 page.
Olsen AL et al. Urethral sphincter needle electromyography in women: comparison of periurethral and transvaginal approaches. Neurourology and Urodynamics, 1998: 17(5) 531-5 (Abstract only) in 1 page.
Pacheco, P; Camacho, MA; Garcia, LI;Hernandez, ME; Carrillo, P; Manzo, J: Electrophysiological evidence for the nomenclature of the pudendal nerve and sacral plexus in the male rat; Brain Research, Jul. 25, 1997, 763(2):202-8. (Abstract only) in 1 page.
Park, K; Golstein, I; Andry, C; Siroky, MB; Krane, RJ; Azadzoi, KM: Vasculogenic female sexual dysfunction: the hemodynamic basis for vaginal engorgement insufficiency and clitoral erectile insufficiency; International Journal of Impotence Research, Mar. 1997, 9(1):27-37. (Abstract only) in 1 page.
Prieto et al. Valsalva minimal leak point pressure: a useful approximation to type III urinary incontinence. Oct. 1998 51(8) 783-9 (Abstract only) in 1 page.
Product Literature for the Impress Softpatch by UroMed Corporation (1998) in 12 pages.
Radziszewski P et al. "The morphological aspects of the innervation of the external urethral striated sphincter." Folia Morphologca, 1995, 54(1):1-7 (Abstract only) in 1 page.
Reliance Urinary Control Insert product literature. UroMed Corporation (1997) in 8 pages.
Roan S. "Campaign Gets Info to Incontinent Women," Los Angeles Times, Apr. 6, 1997 p. E3 in 1 page.
Rocha et al. "Impact of Pregnancy and Childbirth on Female Rats' Urethral Nerve Fibers". J. International Urogynecology vol. 18 No. 12 (2007) (Abstract only) in 1 page.
Salansky, N; Fedotchev, A; Bondar, A: Responses of the venous system to low frequency stimulation and EEG rhythms: clinical implications; Neuroscience and Biobehavioral Reviews, May 1998, 22(3);395-409. (Abstract only) in 1 page.
Search Report and Written Opinion in PCT Application No. US2014/018445 dated Jun. 9, 2014 in 22 pages.
Siltberg et al. Cough-induced leak-point pressure. Acta Obstet Gynecol Scand 77 (1998): 1000-1007 in 8 pages.
Statutory Invention Registration (SIR) No. H1602 to Brock published Oct. 1, 1996 in 8 pages.
Steg. "Urinary Incontinence", p. 266 Churchill Livingstone (1992) in 1 page.
Strohbehn, K; Quint, LE; Prince, MR; Wojno, KJ; Delancey, JO; Magnetic resonance imaging anatomy of the female urethra: a direct histologic comparison; Obstetrics and Gynecology, Nov. 1996, 88(5):750-6. (Abstract only) in 1 page.
Tan et al. Female pelvic floor: endovaginal MR imaging of normal anatomy. Radiology Mar. 1998, 206(3)777-83 (Abstract only) in 1 page.

(56) References Cited

OTHER PUBLICATIONS

Torrens, Chapter 9, "Urodynamics" in Torrens et al. "The Physiology of the Lower Urinary Tract," Springer-Verlag (1987) pp. 277-305 in 29 pages.

Uher et al. "Sacral reflexes: physiology and clinical application." Dis. Colon and Rectum, Sep. 1998, 41(9): pp. 1165-1177 (Abstract only) in 1 page.

Urinary Incontinence in Adults, National Institutes of Health Consensus Development Conference Statement (1988) in 18 pages.

Urinary Stress Incontinence—Awareness Encourages Women to Speak Up, Seek Help (1993), Daniel Freeman Memorial Hospital, in 1 page.

USA Weekend HealthSmart "Can I gain control?—Effective new therapies make living with incontinence easier." p. 14 (2006) in 1 page.

van Buren. "No One Needs to Live with Incontinence," Los Angeles Times, Apr. 6, 1997 p. E4 in 1 page.

Van Duin et al., A computer model of the neural control of the lower urinary tract. Neurourology and Urodynamics, 1998, 17(3): 175-96. (Abstract only) in 1 page.

Von Heyden et al. Neurotransmitters in the human urethral sphincter in the absence of voiding dysfunction. Urol. Res. (1998) 26: 299-310 in 13 pages.

Walker, RJ; Brooks, HL; Holden-Dye, L: Evolution and Overview of Classical Transmitter Molecules and Their Receptors; Parasitology, 1996, 113 Suppl: S3-33. (Abstract only) in 1 page.

Wang et al. Tension-free vaginal tape. A minimally invasive solution to stress urinary incontinence in women. J. Reprod. Med. May 1998, 43(5): 429-34 (Abstract only) in 1 page.

Warrell DW: Pelvic floor neuropathy; in Benson JT (ed): Female Pelvic Floor Disorders. Norton, 1992, Chapter 9, pp. 153-165 in 13 pages.

White R. Incontinence. Encyclopedia Brittanica 1985 Medical and Health Annual pp. 335-338 in 4 pages.

Wyczolkowski M. Functional evaluation of the internal urethral sphincter in transrectal USG. Przeglad Lekarski, 1998, 55(3): 128-32. (Abstract only) in 1 page.

Yilmaz et al. Clitoral Electromyography. J. Urology 167 2:1 (2002) (Abstract only) in 2 pages.

Notice of Allowance mailed May 6, 2016 in U.S. Appl. No. 14/207,259 in 7 pages.

Notice of Allowance mailed May 6, 2016 in U.S. Appl. No. 13/776,930 in 9 pages.

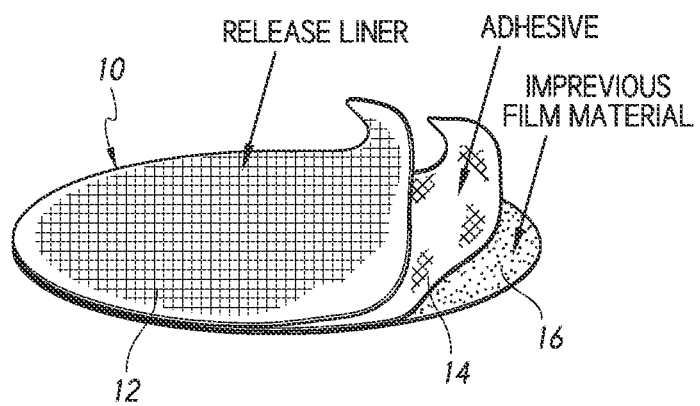
FIG. 1
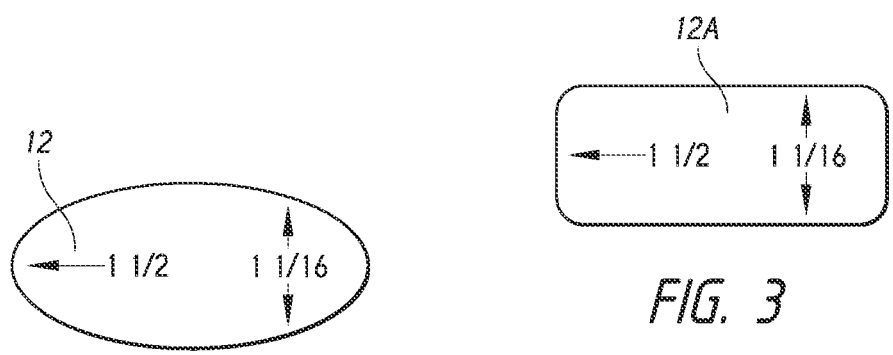
FIG. 2
FIG. 3
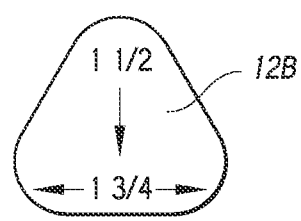
FIG. 4

SYSTEMS AND METHODS FOR TREATING FEMALE INCONTINENCE AND PELVIC NERVE DYSFUNCTION

CROSS-REFERENCE TO RELATED APPLICATIONS

This application is the U.S. National Phase of PCT App. No. PCT/US2014/018445 filed on Feb. 25, 2014, which is a continuation-in-part of application Ser. No. 13/776,930, currently pending, and incorporated by reference in its entirety.

BACKGROUND

Field of the Invention

The indention relates, in some aspects, to systems and methods for treating a pelvic condition, including but not limited to female urinary incontinence.

Description of the Related Art

"Overactive bladder" is defined by the International Incontinence Society as a "symptom syndrome suggestive of lower urinary tract dysfunction." It is specifically defined as "urgency, with or without urge incontinence, usually with frequency and nocturia." Female overactive bladder is a troublesome problem for many individuals. The condition may result from involuntary contraction of the bladder muscle. A number of prescription drugs are used with limited success in treating an overactive bladder and have significant side effects. Other treatments include dietary modification, Kegel instructions and formal physical therapy and different forms of electrical neuromodulation to affect the bladder reflux arc. For those whom these therapies cannot help, there are management modalities of absorbent pads that are used to collect leakage.

A number of devices have been proposed to address female urinary incontinence, represented by, for example, U.S. Pat. No. 5,074,855 to Rosenbluth et al., U.S. Pat. No. 6,131,575 to Lenker et al., U.S. Pat. No. 6,461,340, to Lenker et al., U.S. Pat. No. 3,789,828 to Schulte, U.S. Pat. No. 5,509,427 to Simon et al., U.S. Pat. No. 4,892,535 to Björnberg et al., U.S. Pat. No. 6,179,775 to Thompson, U.S. Pat. No. 6,836,684 to Rijkhoff, and Statutory Invention Registration (SIR) No. H1602 to Brock, the disclosures of each of which are hereby incorporated herein by reference in their entireties. Improved systems and methods for the treatment and prevention of pelvic conditions including but not limited to urinary incontinence are desirable.

SUMMARY

In some embodiments, and not to be limited by theory, disclosed are methods and devices for treating a pelvic condition by applying a stimulus (e.g., a non-electrical, non-magnetic, or a non-electromagnetic stimulus) to one or more clitoral structures sufficient to induce a physiologic stimulatory or inhibitory response. In some embodiments, the methods and devices activate (in a stimulatory or inhibitory manner) one, two, or more types of sensory receptors in a selected anatomical region, such as one, two, or more clitoral structures for example. The sensory receptors could be, for example, mechanoreceptors, nociceptors, proprioceptors, thermoreceptors (e.g., heat and/or cold), hydroreceptors, magnetoreceptors, chemoreceptors, electroreceptors, electromagnetic radiation receptors, and the like, as well as combinations both inclusive and exclusive of any of the foregoing. In some embodiments, the stimulus could exclusively or primarily activate mechanoreceptors. In some embodiments, the stimulus could be mechanical, including one, two, or more of pressure, traction, tension, vibration, and/or friction. In some embodiments, the sensory receptors stimulated are not or are not substantially one or more of: nociceptors, proprioceptors, hydroreceptors, magnetoreceptors, chemoreceptors, electroreceptors, or electromagnetic radiation receptors. In some embodiments, disclosed are methods and devices for treating a pelvic condition by neuromodulating (e.g., reversibly stimulating or inhibiting) neural pathways such as visceral pelvic or somatic nerves of a female person suffering from a pelvic condition associated with nerve dysfunction. Several embodiments of the invention comprise a mechanical stimulation device, such as a neuromodulation device (e.g., a support structure), and methods for using same. The support structure is a patch in some embodiments. A non-electrical, external (outside of the body) and/or internal (e.g., within a body cavity, such as within the vagina or cervix, for example) physical stimulus, such as a mechanical stimulus, can be applied to the clitoral region of the patient according to some embodiments. In some embodiments, the stimulus applied is non-vibratory. Not to be limited by theory, such stimulation can result in neuromodulation. In some embodiments, the device causes a mild local inflammatory response that leads to stimulation of one or more nerves. The pelvic condition of nerve dysfunction can include, for example, female urinary frequency or urgency, overactive bladder, stress, urge, or mixed urinary incontinence, fecal incontinence including retention fecal incontinence, constipation, interstitial cystitis, or pelvic pain, such as vulvodynia, or endometriosis. In some embodiments, the mechanical force exerted by the device is sufficient to result in nerve stimulation to treat a condition such as, for example, incontinence or others as listed above while at the same time not causing or substantially causing female sexual arousal, manifested as, for example, clitoral engorgement or psychological sexual arousal. In other words, the neuromodulation could be to below the level of clinical sexual arousal, e.g., a sub-sexual level of arousal. A temporary and reversible mechanical nerve stimulation device is provided in several embodiments, wherein the device is an adhesive patch that is specifically contoured, shaped and sized to effectively and efficiently apply and maintain pressure and/or apply traction to the clitoral region with a force sufficient to treat female, urinary incontinence. In some embodiments, the device is configured to cause neuromodulation of one, two, or more nerves. In some embodiments, the device includes a therapeutic agent such as a drug, chemical, antibody, or combinations thereof in order to stimulate or inhibit one or more nerves as disclosed elsewhere herein.

In some embodiments, application of mechanical pressure, traction, friction, vibration, or other stimulus to one or more clitoral structures, e.g., using devices and methods as disclosed herein, can inhibit or stimulate nerve activity, including one, two, or more anatomical locations or functional groups as disclosed herein. In some embodiments, devices and methods can be utilized to inhibit peripheral parasympathetic nerve activity and/or promote sympathetic nerve activity in order to relax the detrusor muscle and/or stimulate the urethral sphincter muscles, allowing for bladder filling and treating incontinence, or maintaining continence. Application of a mechanical stimulus to the clitoral structures can, in some embodiments, stimulate tonic inhibition of parasympathetic central nervous system, e.g., by stimulating the pontine continence center in the reticular formation of the pons and inhibiting the pontine micturition center. The striated muscles of the urethra and pelvic floor (e.g. urogenital diaphragm and levator ani muscles), comprising the external urinary sphincter, receive somatic input from anterior horn cells in the S2-S4 segments via the pudendal nerves. These same nerves also contain afferent fibers that play a role in the "guarding reflex". Voiding normally can be voluntarily interrupted by the contraction of the external sphincter. Not to be limited by theory, but application of mechanical pressure, vibration, or other stimulus to the clitoral structures as described herein could block acetylcholine release and/or increase the activity of acetylcholinesterase. Thus, in several embodiments, a device can apply and maintains pressure to the clitoral structure to affect acetylcholine (e.g., including but not limited to inhibiting acetylcholine release and/or increasing degradation of acetylcholine). In some embodiments, the devices and methods disclosed herein can inhibit the reflex voiding center in the sacral spinal cord, such as at the S2-S4 levels. Neurons in the intermediolateral cell column can supply parasympathetic excitatory input to the detrusor muscle via the pelvic nerves and plexuses. These fibers synapse in ganglia near or within the bladder wall. Afferent inputs can also be transmitted via the pelvic nerves mainly through the S2-S3 roots. Sensations of proprioception (distention), pain, and temperature are conveyed by these fibers, which give rise to the sensation of the desire to void, are carried by the spinothalamic tracts as well as the posterior columns. Any one, two, or more of the foregoing anatomical structures or groups of structures could be stimulated or inhibited using system and methods as disclosed herein.

In contrast to medications for incontinence such as, e.g., oxybutynin that could potentially have unwanted systemic anticholinergic effects such as, for example dry mucous membranes, constipation, dizziness, tachycardia, confusion, and the like, systems and methods as disclosed herein can advantageously provide, in several embodiments, a local targeted effect on bladder control musculature without the aforementioned systemic side effects. Furthermore, in contrast to botulinum toxin which is injected directly into the bladder via a procedure such as cystoscopy, systems and methods as disclosed herein can advantageously function, in several embodiments, via a non-invasive approach. Thus, in some embodiments, the invention comprises a device or method for treating a pelvic disorder (such as incontinence) that does not utilize an oral or injected medication or toxin. According to several embodiments, the invention provides non-invasive reversible mechanical neuromodulation, and not, for example, chemical or thermal neuromodulation.

In some embodiments, a topical formulation for the treatment of a pelvic condition, such as stress, urge, and/or mixed urinary incontinence for example, is disclosed. The formulation can comprise, or consist essentially of an amount of a biocompatible medical adhesive sufficient for application to a clitoral structure, and can be provided independently or on a device. The amount of the formulation applied is sufficient to apply mechanical pressure to a clitoral structure such that one or more clitoral nerves will be neuromodulated to a sub-sexual arousal level. The formulation can comprise, in some embodiments, between about 90% and about 97% by weight of an acrylic polymer, and between about 3% and 10% by weight of an acrylic acid. The acrylic polymer can be selected from the group consisting of isooctyl acrylate, 2-ethyl hexyl acrylate, isononyl acrylate, decyl acrylate, dodecyl acrylate, butyl acrylate, hexyl acrylate, and mixtures thereof. The formulation can be configured such that when it is removed from the clitoral structure less than about 20%, or less than 10% of the adhesive surface area is covered by detached skin cells of the patient. In some embodiments, the device is physically removable by a user. In other embodiments the device dissolves, or loses adhesiveness sufficient to naturally detach from the skin after a preselected time period while operably attached to the user, or after removal when placed in the trash or toilet, for example. In some embodiments, the adhesive will be at least partially resistant to water, therefore allowing bathing and normal urination while remaining intact. In yet other embodiments, the device is implanted on a weekly, monthly, quarterly basis or longer and is controlled (e.g., electronically and wirelessly) by the user. In other words, a user can wirelessly control the amount of pressure, vibration, or other stimulus placed on the clitoral shaft in order to control incontinence. Clitoral cuffs around the glans and/or shaft, for example, that can be expanded and relaxed to modulate pressure (and thus control neuromodulation), are provided in several embodiments.

The topical formulation, in some embodiments, could comprise between about 50% and about 97% by weight of an acrylic polymer (e.g., 50-60%, 60-70%, 70-80%, 80-97%, and overlapping ranges thereof), and between about 3% and 50% (e.g., 3-20%, 20-30%, 30-40%, 40-50%, and overlapping ranges thereof) by weight of an acrylic acid. The topical formulation could also include a silicone adhesive, such as a polydiorganosilexane, and a copolymeric silicone resin. The moisture vapor transmission rate of the formulation when applied can be about or greater than about 400 g/m$^2$, 500 g/m$^2$, 600 g/m$^2$, 1000 g/m$^2$, 2000 g/m$^2$, 3000 g/m$^2$, 4000 g/m$^2$, 4200 g/m$^2$, 4500 g/m$^2$, 5000 g/m$^2$, or more.

Also disclosed herein are devices, e.g., patches for treating a pelvic condition of a female patient. The devices can include an adhesive layer sized and configured for application at least between e.g., also spanning the labia majora), or exclusively between opposing folds of the labia majora. The device when applied can be configured to directly contact and adhere to the skin of one or more clitoral structures selected from the group consisting of: the clitoral shall, clitoral hood, and the clitoral glans. The device when applied can be configured to apply a mechanical force, vibration, or other stimulus to the clitoral structures sufficient to stimulate, e.g., neuromodulate one or more clitoral nerves while not causing sexual arousal. The adhesive layer can comprise an adhesive configured such that when removed from the clitoral structures less than about 20%, 10%, or less of the adhesive surface area is covered by detached skin cells of the patient. In some embodiments, the weight of the adhesive layer per surface area of the device can be in the range of about 7 g/m$^2$ to about 100 g/m$^2$ (e.g., 7-20 g/m$^2$, 20-30 g/m$^2$, 30-40 g/m$^2$, 40-50 g/m$^2$, 50-75 g/m$^2$, 75-100 g/m$^2$, and overlapping ranges thereof). In some embodiments, the device can be between about 0.5 inches and about 3 inches long (e.g., 0.5-1 inches, 1-2 inches, 2-3 inches, and overlapping ranges thereof) at its longest, between about 0.5 inches and about 2 inches wide (e.g., 0.5-1 inches, 1-1.5 inches, 1.5-2 inches, and overlapping ranges thereof) at its widest, and/or have a thickness of between about 0.0001 inches and about 0.1 inches (e.g., 0.0001-0.001 inches, 0.001-0.01 inches, 0.01-0.1 inches, and overlapping ranges thereof) at its thickest point. In some embodiments, the adhesive can be configured to decouple from the patient's clitoral structures within about 6, 12 or 24 hours, and/or biodegrade within about 6, 12 or 24 hours. The device can include a backing layer coupled to the adhesive layer. The backing layer can comprise a flexible film material. The device can also include one or more features selected from the group consisting of a contoured portion, a raised portion, a tab, a malleable portion, and any combination thereof. Any of the foregoing portions can be configured to facilitate maintenance of the mechanical force on the one or more clitoral structures while the patient is at rest and/or during activity. The contoured portion can have a curvature of between, for example, about 10% and about 30% along an axis of the device. wherein the raised portion encompasses the center of the contact surface of the support structure. The contact surface can include the raised portion having a surface area and a non-raised portion having a surface area. The raised portion can have a surface area that is, for example, between about 10% and about 100% of the surface area of the non-raised portion. The raised portion can have a maximum thickness that is at least about 10%, 20%, 30%, 40%, 50%, or more greater than the thickness of a non-raised portion of the device. The device can also comprise one or more protrusions configured to apply mechanical force to the clitoral structures, and/or one or more depressions configured to apply a radial mechanical force to the clitoral structures. The device can also include one or more stiffening members, which may comprise a shape memory material in some cases. The stiffening members can extend around at least a portion of the perimeter of the device. The adhesive layer has a surface area of between about 1 square inch and about 2 square inches. In some cases a device comprises one, two, or more laterally, anteriorly, or ventrally extending tabs to facilitate grasping the device, e.g., patch. In some embodiments, the tab does not contain any adhesive to facilitate application and removal of the device. The adhesive can comprise an acrylic component, such as, for example, between about 50% and about 98% by weight of an acrylic polymer and between about 2% and about 50% by weight of an acrylic acid. The adhesive can include a hydrocolloid component, and/or a silicone component. The device can also comprise an absorbent material coupled to the backing layer. In several embodiments, a device is provided to apply a mechanical stimulus, e.g., pressure, tension, friction, traction, and/or vibration to the clitoral structure with a force that is exerted on the tissue to maintain sufficient contact and stimulus for at least 0.5, 1, 6, 12, 24, 48 and 72 hours (e.g., between about 0.001-0.01 g/mm$^2$, 0.01-0.1 g/mm$^2$, 0.1-0.5 g/mm$^2$, 0.5-1 g/mm$^2$, 0.1-1 g/mm$^2$, 1-5 g/mm$^2$, 5-10 g/mm$^2$, and overlapping ranges thereof). In many embodiments, these pressure ranges are applied consistently over a desired time period (e.g., over the course of hours or days).

Also disclosed herein is a device as described herein, and a urethral plug device comprising a tubular body configured to fit within the urethra of the patient. The device can be coupled to, or separate from the urethral plug device. Further disclosed herein is a device for treating a pelvic condition of a female patient that includes an adhesive layer sized and configured for application to the clitoris or the clitoral hood. The device when applied can be configured to apply a mechanical stimulus to the clitoris or the clitoral hood sufficient to neuromodulate a clitoral nerve. The adhesive layer can comprise a pressure-sensitive acrylic adhesive, and can also include a tab to facilitate holding the device.

A kit is also disclosed, comprising a plurality of patches, a dispenser, a mirror, and/or a housing. In some embodiments, the patches can be arranged linearly on and releasably connected to a release sheet having perforations between each patch, the release sheet configured to form a roll. The kit can further comprise a dispenser configured to house the roll. In several embodiments, the invention comprises several devices to apply a mechanical stimulus, e.g., pressure and/or traction (e.g., patches) and instructions to apply the device to the clitoral region.

In some embodiments, disclosed herein is a method for treating a pelvic condition (including, but not limited to, urinary incontinence) of a patient. The method can include applying mechanical stimulus, e.g., pressure, intermittently or continuously, to one or more clitoral structures, including the clitoral shaft, clitoral hood, and the clitoral glans for example. The method can also involve applying a device to one or more clitoral structures, the device being sufficiently malleable to stably conform to a shape of the one or more clitoral structures. The method can also include deforming at least a portion of the device from a first configuration to a second configuration, the second configuration conforming to the shape of the one or more clitoral structures sufficient to apply a mechanical stimulus to one or more clitoral structures. The applied mechanical stimulus can be sufficient to neuromodulate one or more clitoral nerves to treat a pelvic condition while not causing sexual arousal. The stimulus can be applied for at least about 2 hours, 4 hours, 8 hours, 12 hours, 24 hours, several days, or more. The pelvic condition can be one or more of female urinary frequency, urgency, overactive bladder, stress urinary incontinence, urge urinary incontinence, or mixed urinary incontinence, urinary retention, fecal incontinence, constipation, interstitial cystitis, vulvodynia, and endometriosis. Applying mechanical stimulus to the one or more clitoral structures can comprise applying a device comprising an adhesive layer to the clitoral structures. The adhesive layer can comprise an adhesive configured such that when removed from the clitoral structures less than about 20%, 10%, or less of the adhesive surface area is covered by detached skin cells of the patient. Applying mechanical stimulus to the one or more clitoral structures can also comprise securing a device, such as a clamp for example, against the one or more clitoral structures. The device can be carried by a panty, sanitary napkin, or another garment. The method can also include inserting a urethral plug into the urethral opening of the patient. The mechanical stimulus applied can be sufficient to neuromodulate a branch of the pudendal nerve and/or the cavernous nerve.

In some embodiments, systems and methods as disclosed herein do not necessarily need to include an absorbent pad to catch urine or trap urine in the bladder, need to be inserted into a body cavity, have a rigid or semi-rigid component, or projections, or require electronic components such as an electronic impulse generator, although in some embodiments the foregoing features can be included as well. In some embodiments, devices can be used during intercourse without needing to be removed.

In some embodiments, mechanical pressure, traction, vibration, friction, or other stimulus is applied noninvasively to the clitoral region, for example, the clitoral hood, by a substance adapted to be secured over the clitoral region. In one embodiment, the substance comprises a device with adhesive and is applied to the clitoral region. Traction provided by the device can be sufficient to stimulate the nerves of the clitoral region. The adhesive can be on both or either side of a backing sheet formed of a flexible material. The flexible material can, in some embodiments, have a thickness of from about 0.012 mm to about 0.051 mm (e.g., about 0.012-0.02 mm, about 0.02-0.05 mm, and overlapping ranges thereof) with an adhesive layer on a backing sheet, the adhesive layer being suitable for application directly to the clitoral region, the device being shaped so as to cover the clitoral region. In one embodiment, the thickness is about 0.02 mm. A release sheet can be provided to protect the adhesive layer from drying out before use. In another embodiment, the device has adhesive on one side of a backing sheet. A plurality of such patches can be arranged linearly, connected by tear lines. Optionally, a small cloth or paper tab can be secured by the adhesive at a leading edge of the patch to facilitate handling. The linear arrangement of patches can be mounted in a dispenser so configured so that single patches can be withdrawn from the dispenser aided by pulling on the tab, which also serves to act as a stop in drawing the patch from the dispenser.

In another embodiment, a solid object, which can be pliable, is secured against the clitoral region. The solid object, for example a solid curvilinear plastic member can be secured to the adhesive or be under the adhesive, e.g., secured to the front side of a backing sheet having an adhesive layer on the front side whereby the solid object can be applied directly to the clitoral region to apply a stimulus, e.g., physical pressure thereon. Other shapes are used in accordance with other embodiments.

In still another embodiment, the solid object can be mounted on the inside of a supportive garment, such as a panty, in a location such that in wearing the panty, the solid object will be applied to the clitoral region to apply a stimulus, e.g., physical pressure thereon.

Some embodiments of the invention provide a simple, low cost solution to a vexing problem, making therapy more safe, affordable and available. Certain embodiments can be designed to comfortably fit almost any human female who suffers from urinary frequency or urgency and includes the necessary elements that compliment comfort, ease of use and confidence. The device, for example, is produced with soft, pliable materials that allow the user to continue daily routines without discomforts or embarrassing interruptions. With the possible exception of a person requiring assistance with certain basic activities of daily living, who would have the device applied by someone else, some embodiments are designed to permit the user to apply the device without any assistance.

The device can be produced in various sizes, e.g., small, medium, and large to accommodate variance in patient anatomy. It is well suited for minimally active to highly active women, e.g. engaging in running, jogging, high or low impact aerobics or any exercise where movement of the lower torso is essential. The product can be very portable and can be available in individually sealed and sterilized packages of multiple units, which can easily fit into the average purse or pouch. The cost, comfort, simplicity, portability and ease of use attributed to this device, can potentially surpass other products presently available either by prescription and/or the consumer over-the-counter market.

BRIEF DESCRIPTION OF THE DRAWINGS

FIG. 1 is a perspective view of an embodiment of a device configured to reversibly attach to a clitoral structure, shown with portions peeled up to better illustrate its construction;

FIG. 2 is a top plan view of the device of FIG. 1;

FIG. 3 is a top plan view of a device similar to that of FIG. 1, but having a rectangular shape;

FIG. 4 is a top plan view of a device similar to the device of FIG. 1, but having a triangular shape;

DETAILED DESCRIPTION

Figure 4A:
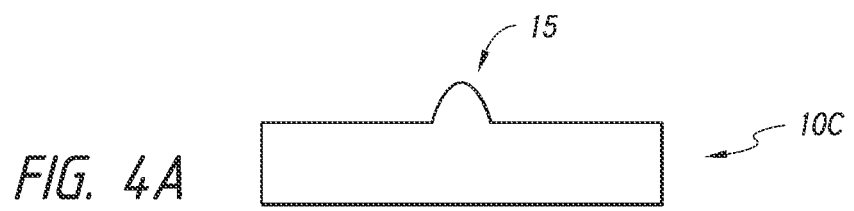
FIG. 4A is a side view of an embodiment of a device having a protrusion.

In some embodiments, disclosed herein are devices that can treat or prevent a pelvic condition, such as stress, urge, or mixed urinary incontinence, or others as disclosed elsewhere herein. The devices could take the form of a patch in some cases and include a backing sheet, one, two or more adhesive layers that may have the same or different degrees of adhesiveness, and a release layer.

Referring to FIGS. 1 and 2, a generally oval patch 10 is shown formed of a backing sheet 16 coated with one, two, or more layers of adhesive 14 and covered with a release sheet/layer 12. The adhesive layer 14 in some embodiments can be pressure sensitive and non-allergenic. In some embodiments having a plurality of adhesive layers, the first adhesive layer has an adhesion strength that is greater than or equal to about 5%, 10%, 15%, 20%, 25%, 30%, 35%, 40%, 50%, 75%, 100%, or more than that of the second adhesive layer. Either the first adhesive layer or the second adhesive layer could be directly proximate the skin surface. In some embodiments, the first adhesive layer is proximate the backing sheet and the second adhesive layer is sprayed on directly to the skin or the second adhesive layer.

A patch 10 can be, for example, between about 1 inch and about 3 inches in length at its longest portion, between about 1 inch and about 2 inches in length (e.g., about 1 inch, about 1.25 inches, about 1.5 inches, about 1.75 inches, or about 2 inches in length), between about 1 inch and about 1.5 inches in length, between about 1.5 inches and about 2 inches in length, between about 1.25 inches and about 1.75 inches in length, between about 1.4 inches and about 1.6 inches in length, or approximately 1½ inches in length in one embodiment. The patch 10 can be, for example, between 0.5 inches and 2 inches in width, between about 0.75 inches and about 1.5 inches in width, between about 0.75 inches and about 1.25 inches in width, or about ¾, 13/16, ⅞, 15/16, 1, 1 1/16, 1 1/18, 1 3/16, or 1¼ inches wide at its widest in one embodiment. The patch (e.g., all layers of the patch together), in some embodiments, could have a mean thickness, or thickness at its thickest portion of between about 0.0001 inches and about 0.1 inches, between about 0.0004 inches and about 0.004 inches, between about 0.007 inches and about 0.013 inches, or about 0.008 inches, 0.009 inches, 0.010 inches, 0.011 inches, or 0.012 inches. The patch could have a constant, substantially constant, or variable thickness throughout. In some embodiments, the patch could be configured to stretch/elongate by about or at least about 20%, 30%, 40%, 50%, 60%, 70%, 80%, 90%, 100%, 150%, 200%, 300%, or more. The patch could be die-cut, or formed by other manufacturing techniques, some of which are disclosed elsewhere herein.

In some embodiments, the device, e.g., the patch could also include one, two, or more therapeutic agents coated or otherwise operably attached thereon. The therapeutic agent could be an anesthetic agent in some embodiments, for comfort while the device is applied as well as when it is removed. The anesthetic agent could be, for example, lidocaine, bupivacaine, or a combination thereof. In some embodiments, the therapeutic agent could also be a hormone, such as an estrogen or progesterone for example. In some embodiments, the therapeutic agent could be a sympathetic nervous system agonist or antagonist, or a parasympathetic nervous system agonist or antagonist. In some embodiments, the therapeutic agent could be oxybutynin or a botulinum toxin.

The backing sheet 16 can be a film material and manufactured from a thin, flexible plastic film, although other flexible liquid materials may also be used. As used herein, the term "flexible" refers to materials which are compliant and will readily conform to the general shape and contours of the clitoral region. The backing sheet 16 material may as described for the backsheet material of Statutory Invention Registration (SIR) No. H1602 to Brock, incorporated herein by reference. In some embodiments, the backing sheet comprises a woven or nonwoven material, polymeric films such as thermoplastic films of polyethylene or polypropylene, and/or composite materials such as a film-coated nonwoven material, illustrated by a polyethylene film having a thickness of, for example, from about 0.005 mm to about 0.01 mm, or from about 0.012 mm to about 0.051 mm. In some embodiments, the backing sheet 16 or other components of the patch can include one, two, or more absorbent materials, in order to absorb moisture, e.g., absorb sweat, vaginal fluids, or any urinary leakage. The absorbent material could include, for example, natural or synthetic silk fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers, acetate fibers, and combinations thereof. In some embodiments, the absorbent material could have an absorbency of about or at least about 10 g/g, 15 g/g, 20 g/g, 25 g/g, or more.

The release layer/sheet 12 can keep the adhesive from drying out and can be formed of an adhesive releasing material. Other non-limiting examples of the adhesive releasing material/sheet includes paper, resin film, nonwoven fabric, and nonwoven fabric laminated with resin film, each having been treated with silicone. The release layer is removed before applying the patch 10.

FIG. 3 shows a patch 10A similar to the patch of FIG. 1, but having a generally rectangular shape about 1½ inches long and about 1 and 1/16 inches wide in one embodiment, although other dimensions as described herein are also possible.

FIG. 4 shows a patch 10B similar to the patch of FIG. 1, but having a generally triangular shape about 1½ inches high and about 1 and ¾ inches at its base in one embodiment, although other dimensions as described herein are also possible.

While generally oval, rectangular, and triangular patches (with or without rounded edges) are described and illustrated above, a device, such as a patch can have any appropriate shape (from either a top view, or a cross-sectional view) or dimensions so long as it is configured to cover, and/or exert a mechanical stimulus, e.g., pressure on at least a portion of the clitoral region, including the clitoral glans and/or clitoral hood. In some embodiments, the patch could have a generally arcuate shape, such as a circle; half-circle, square, rhomboid, lobed (e.g., butterfly), hourglass, hexagonal, starburst, or irregular shape for example, or any of the foregoing with radially, axially, or otherwise extending tab or wine portions. In some embodiments, the one, two, or more tab portions can have a length of between about 0.25 inches and about 1 inch, between about 0.25 inches and about 0.75 inches, between about 0.25 inches and about 0.5 inches, between about 0.5 inches and about 0.75 inches, between about 0.75 inches and about 1 inch, about 0.25 inches, 0.5 inches, 0.75 inches, about 1 inch, and overlapping ranges thereof. In some embodiments, the one, two, or more tab portions can have a width of between about 0.25 inches and about 1 inch, between about 0.25 inches and about 0.75 inches, between about 0.25 inches and about 0.5 inches, between about 0.5 inches and about 0.75 inches, between about 0.75 inches and about 1 inch, about 0.25 inches, 0.5 inches, 0.75 inches, about 1 inch, and overlapping ranges thereof. In some embodiments, the patch can be any desired shape and have a surface area sufficient to partially or entirely cover the clitoral glans and/or clitoral hood, such as between about 0.5 square inches and about 4 square inches, between about 1 square inch and about 2 square inches, between about 1 square inch and about 1.25 square inches, between about 1.25 square inches and about 1.75 square inches, or about 1.25 square inches, about 1.5 square inches, or about 1.75 square inches in some embodiments. The patch could be dimensioned to avoid covering a patient's urethra, although a patch could cover at least a portion of, or the entirety of the patient's urethra in other embodiments. The patch can, in one embodiment, be contoured in one more regions, including having a curvature of about 10-30% (e.g., about 10%, 15%, 20%, 25%, or 30%) along an axis of the patch. In some embodiments, the patch is contoured in one, two, or more dimensions, such as a length, width, and or thickness dimension. In some embodiments, the entire device or portions thereof can have a high malleability (that is, it deforms under stress and does not return to its original shape when the stress is removed) to establish or maintain a force on one or more clitoral structures. In some embodiments, the entire device or portions thereof have a high ductility (able to deform under a tensile strength without breaking). In some embodiments, the device is able to elongate in one, two, or more directions (e.g., length, width, and/or thickness) by about or at least about 5%, 10%, 15%, 20%, 25%, 30%, 35%, 40%, 50%, 60%, 75%, 100%, 200%, 300%, or more without partially or completely fracturing. In some embodiments, the device can be applied to one or more clitoral structures, and at least a portion of the device can be sufficiently malleable to stably conform to a shape of the one or more clitoral structures, and/or apply a force sufficient to neuromodulate the one or more clitoral structures at a sub-sexual arousal level. A device or at least a portion of the device can be deformed from a first configuration to a second configuration, the second configuration conforming to the shape of the one or more clitoral structures sufficient to apply mechanical stimulus, e.g., pressure or traction to one or more clitoral structures.

In some embodiments, as illustrated in the side schematic view of FIG. 4A, the patch 10C could have one, two, or more raised or depressed areas, such as protrusions 15 or ridges, such as in a central area, at or about the centroid of the device, or proximate one, two, or more corners of the patch 10C, or around the entire perimeter, or about or at least about 10%, 20%, 30%, 40%, 50%, 60%, 70%, 80%, or more around the perimeter of the device for example. The protrusions 15 can be formed, for example, in a region where the backing sheet and/or adhesive layer has an increased thickness relative to another region of the backing sheet and/or adhesive layer, and advantageously applies increased stimulus, e.g., pressure and/or better maintains the stimulus on the anatomical region of interest when the patient is at rest, and/or moves or changes position for example. In some embodiments, the device provides a stimulus, e.g., pressure and/or traction when the patient is at rest only (static stimulus, e.g., pressure), while moving only, e.g., ambulating (motion stimulus, e.g., pressure), or while both at rest and while moving. In some embodiments, as illustrated in the schematic side view of FIG. 4B, the patch 10D could include one, two, or more depressions 17, such as in a central area of the patch for example. When the patch 10D is molded to the female anatomy, the depressions 17 can allow the patch to additionally exert, for example, radial and/or circumferential pressure on the clitoral glans and/or hood, such as in the direction of arrows. In some embodiments, the device, such as a patch could have a base surface area and a raised and/or depressed surface area having a thickness different than the thickness of the base surface area, wherein the ratio of the raised and/or depressed surface area to the base surface area is about or at least about 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.5:1, 3:1, or more. In some embodiments, the device, such as a patch could have a raised area having a thickness that is at least about or about 105%, 110%, 115%, 120%, 125%, 130%, 135%, 140%, 145%, 150%, 175%, 200%, or more compared with the thickness of a non-raised area of the device. In some embodiments, the raised area may comprise a second adhesive having properties different from the first adhesive, including different adhesive properties. In some embodiments, the device, such as a patch could have a raised or depressed area having a thickness that is at least about or about 0.0005 inches, 0.001 inches, 0.002 inches, 0.003 inches, 0.004 inches, 0.005 inches, 0.006 inches, 0.007 inches, 0.008 inches, 0.009 inches, 0.010 inches, 0.015 inches, 0.02 inches, 0.03 inches, 0.04 inches, 0.05 inches, 0.1 inches, or more greater than that of the thickness of the non-raised area of the device, in some embodiments, the raised or depressed areas could have a generally conical, pyramidal, cubical, or other desired geometry, and/or dimensioned to apply selective additional stimulus, e.g., pressure or traction (relative to the non-raised or depressed area of the device) to a clitoral structure, such as the clitoral glans, shaft, or hood, for example, without substantially applying selective additional stimulus, e.g., pressure or traction to an adjacent non-clitoral structure. In some embodiments, a device could have one, two, or more apertures sized and configured such that at least a portion of one or more clitoral structures is confined within the aperture, and the device applies traction in an appropriate direction such that the portion of the one or more clitoral structures is pulled anteriorly, ventrally, or laterally for example sufficient to neuromodulate one or more nerves, such as clitoral nerves or others as disclosed herein.

Figure 4B:
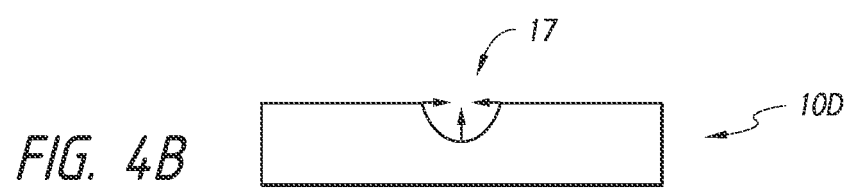
FIG. 4B is a side view of an embodiment of a device having a depression.
Figure 4C:
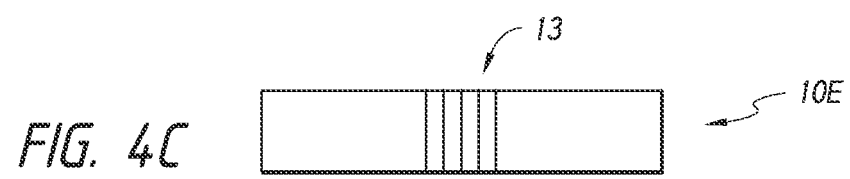
FIG. 4C is a top view of an embodiment of a device having one or more stiffening members.
Figure 4D:
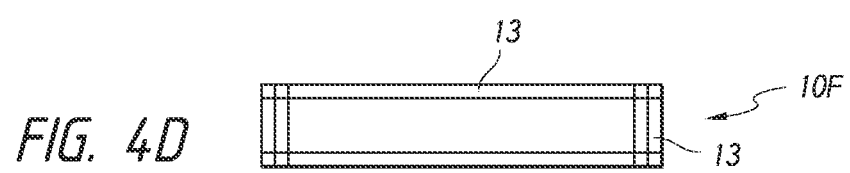
FIG. 4D is a top view of an embodiment of a device having stiffening members oriented around the perimeter of the device.

In some embodiments, as illustrated in the schematic top view of FIG. 4C, the patch 10E can include one, two, or more stiffening members 13 oriented longitudinally as illustrated, or axially, diagonally, or otherwise. FIG. 4D illustrates in a schematic top view an embodiment of a patch 10F with stiffening members 13 spaced around the perimeter of the patch 10F. The stiffening members 13 can be placed, for example, proximate the adhesive layer and thus directly contacting the patient's anatomy, in between the adhesive layer and the backing layer, or on the backing layer on the surface furthest away from the patient's anatomy. The stiffening members 13 may be made of any appropriate material, such as plastic, a metal, or a shape memory material such as a shape memory metal or polymer for example, and be configured to be malleable and/or moldable to apply additional stimulus to the anatomic site of interest, such as the clitoral glans and/or hood.

Figure 4E:
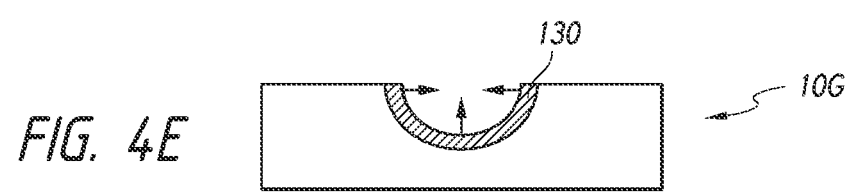
FIG. 4E is a side view of an embodiment of a device having a biasing member.

FIG. 4E illustrates a side schematic view of an embodiment of a patch 10G having a depression 17 as shown in FIG. 4B, with a biasing member 130, such as a shape memory metal or polymer, configured to exert additional radial and/or circumferential pressure on the anatomical site of interest, such as the clitoral glans and/or hood. In some embodiments, the biasing member 130 could take the form of a partial or a full ring.

Many adhesives currently used in connection with dressings for skin and wound-care bond tenaciously to skin and other tissue. The level of bond strength can build up even after just a few hours of wear. The sensory perception felt when peeling back such adhesives that have had even just a few hours to dwell on the skin can be quite painful and can cause damage to, for example, the epidermal layer of the skin or other epithelium. Pain can be caused by trauma to the skin by way of induced edema and/or erythema.

Furthermore, adhesives repeatedly and chronically applied to the same site of the body, resulting in repeated removal and reapplication of the adhesive. When repeatedly applied and removed, such adhesives are apt to remove with them parts of the skin or other epithelial layers. The damage to the tissue can manifest in an increase in transdermal water loss. These adhesives also fasten strongly to hair, which can add to the discomfort and irritation experienced when the adhesive is removed. Additionally, the tissue layer stripped by the adhesive during removal deadens the tack and the adhesive properties, thus diminishing the reapplication potential of the adhesive.

As such, it can be desirable to utilize adhesives that can be removed from tissue with little to no pain and with little or no trauma to skin but which also can easily be reapplied or repositioned and resists edge rolling when used in conjunction with a tape, patch, or other article. The adhesives can be configured to provide the ability to lift-up a patch temporarily and then to re-attach the adhesive without relevant loss in adhesive strength. This also allows a patient to rework the adhesive patch in case it is misapplied or folds over on itself.

It can be desirable in some embodiments to utilize adhesives in which the pain experienced on removal is low, even after up to 1, 2, or more days of wear; the adhesion does not significantly build with time; does not cause maceration of the skin; and/or the surface of the adhesive is substantially free of skin or other epithelial cells when the adhesive is peeled back.

Biocompatibility of adhesives can be characterized by cytotoxicity, skin irritation, and skin sensitization. The cytotoxicity of adhesives in accordance with some embodiments does not exceed 2 when using the Organization for international Standardization (ISO, e.g., ISO 10993) agarose overlay method; the cytotoxicity can be less than 1, such as zero. The skin irritation, using the ISO skin irritation rating, in some embodiments does not exceed 2 and could be less than or equal to 1, 0.8, 0.5, or 0.4 (non-irritating). Adhesives in accordance with exemplary embodiments do not act as skin sensitizers under Globally Harmonized System for Classification and Labeling of Chemicals (GHS) standards.

Certain embodiments result in adhesive compositions that can be applied to skin, either independently of or in conjunction with the application of a patch, dressing, affixing tape, or other medical device adhered to the skin and that can be subsequently removed with little or no pain. Although pain experienced during adhesive removal can be difficult to measure precisely as it can be influenced by a wide range of factors, the Wong-Baker pain scale is recognized in the medical field to quantify pain intensity measurement. This 0 to 5 scale, with 5 being the highest pain level, is often used to gauge the pain experience of an individual. Some embodiments of adhesives achieve an average Wong-Baker pain rating of less than about 2.5 during adhesive removal even after up to 2 hours, 3 hours, 4 hours, 6 hours, 12 hours, 18 hours, 1 day, 2 days, or more of wear. In some embodiments, the average Wong-Baker pain rating during adhesive removal is less than about 2.0, 1.5, 1.0, or even less.

Some adhesive bond failures occur when peeling the adhesive from skin does not take place at the adhesive-skin interface but instead the failure takes place at the interface between the upper layer of skin cells and the dermis. This is signified by the large quantity of skin cells fouling the peeled-back adhesive. Therefore, the force required to remove the adhesive from the skin is essentially the same as the force at which the adhesive pulls off large amounts of skin cells from the dermis layer (i.e., resulting in trauma to the skin and thus translating to pain felt by the wearer). In some embodiments, the adhesive bond failure occurs at the adhesive-skin interface which is signified by none or very little skin cells attached to the adhesive. Using this underlying difference in the mechanism of bond failure when peeling from skin, adhesives can possess both high peel and low pain upon removal.

Adhesives in accordance with certain embodiments have a stripping effect of less than 50%, that is, they are capable of being removed from the skin with less than 50% of the adhesive surface area being fouled by detached skin cells and typically the stripping effect is less than about 40%, 30%, 20%, 10%, 5%, or even less. In some embodiments, the stripping effect is less than about 10%, such that up to 90% or more of the previous bonding force is available so that the adhesive can be repositioned and re-attached to the skin. Furthermore, the removal of fewer skin cells can correlate to less pain experienced by the wearer.

Some embodiments also result in an adhesive that has suitable wear performance. If the peel is reduced too much, then the adhesive deteriorates in wear properties, that is, it tends to roll off or fall off prematurely. In some embodiments, the adhesive is sufficiently adherent to releasably bond to the skin for about, or no more than about 72 hours, 48 hours, 24 hours, 18 hours, 15 hours, 12 hours, 11 hours, 10 hours, 9 hours, 8 hours, 7 hours, 6 hours, 5 hours, 4 hours, 3 hours, or 2 hours. The peel force can be, in some cases, as close to, but not over, the amount of force required to remove a majority of skin cells from the area of the skin in contact with the adhesive, although it will be appreciated that force can vary slightly from person to person, based on skin type, weather conditions and diet, for example.

In order for the adhesive dressing or affixing tape for skin applications to function effectively, the force with which the adhesive adheres to the skin should exceed the load to which it is subjected during normal use. The peel force can be on the order of 0.2 N force per centimeter of width when peeling or stripping at an angle of 90° from the skin. In some embodiments, the force is more than 0.3 N/cm, 0.6 N/cm, 0.8 N/cm, 1.0 N/cm, or more, which allows for samples to bond to the skin for several days. In some embodiments, peel force is 0.6 N/cm using a 1 hour dwell and over 0.8 N/cm after a 24 hour dwell on the skin. In some embodiments, in adhesion to bright, annealed #302 or #304 ANSI stainless steel according to ASTM standard adhesion testing procedures, when peeling or stripping at an angle of 90° or 180°, the adhesive could have, for example, the following properties: about 12-16 ounces/inch width, e.g., about 12, 13, 14, 15, or 16 ounces/inch width about 340-460 gms/25 mm, e.g., about 340, 350, 360, 370, 380, 390, 395, 397, 400, 403, 405, 410, 420, 430, 440, 450, or 460 gms/25 mm) (about 3.5-4.5 N/25 mm, e.g., about 3.5, 3.6, 3.7, 3.8, 3.9, 4.0, 4.1, 4.2, 4.3, 4.4, or 4.5 N/25 mm) or overlapping ranges thereof.

One method of quantifying wear performance is edge lift. Edge lift is a measure of the percentage of the total area of a patch to which adhesive has been applied that is no longer bonded to the skin during the wear-time. Some embodiments achieve less than 10%, 8%, 5%, 3% or less edge lift occurring over a 2, 4, 6, 8, 12, 18, or 24 hour period.

Adhesives in accordance with certain embodiments can exhibit relatively high moisture vapor transmission rates (MVTR). In some embodiments, the MVTR can be greater than or equal to about 400 $g/m^2$, 500 $g/m^2$, 600 $g/m^2$, 700 $g/m^2$, 800 $g/m^2$, 900 $g/m^2$, 1000 $g/m^2$, 1100 $g/m^2$, 1200 $g/m^2$, 1300 $g/m^2$, 1400 $g/m^2$, 1500 $g/m^2$, 2000 $g/m^2$, 2500 $g/m^2$, 3000 $g/m^2$, 3500 $g/m^2$, 4000 $g/m^2$, 4500 $g/m^2$, 5000 $g/m^2$, or more per day for example. In some embodiments, the MVTR could be between about 3500 $g/m^2$ and 5000 $g/m^2$, between about 4000 $g/m^2$ and 4500 $g/m^2$, or about 4200 $g/m^2$ per day, or overlapping ranges thereof. This can be an advantage in some embodiments to allow the skin to breathe. Adhesives that do not breathe can, in some cases, accumulate moisture at the skin-adhesive interface which in turn leads to maceration of the skin. Macerated skin becomes weak and it can easily tear and cause pain when the adhesive is removed. Accumulation of moisture also can potentially promote bacterial growth on the skin.

Patches and other devices making use of adhesives in accordance with some embodiments can also exhibit little or no sliding or creep from the application site. They remove cleanly, leaving little to no residue on skin or clouting, even if contacted by fluids (e.g., water, isopropanol, wound exudate, etc).

The adhesive layer can comprise, or consist essentially of a hydrophilic adhesive composition which may be sticky, viscous gel, or a substantially solid composition. The adhesive layer can also include one, two, or more pressure sensitive adhesives (PSA) such as tackified rubber adhesives, such as natural rubber, olefins, silicones, polyisoprene, polybutadiene, polyurethanes, styrene-isoprene-styrene and styrene-butadiene-styrene block copolymers, and other elastomers; vinyl esters and amides, and tackified or untackified acrylic or methyacrylic adhesives such as copolymers of isooctylacrylate and acrylic acid, and/or ester homopolymers or copolymers. The adhesives can be polymerized by radiation, solution, suspension, or emulsion techniques. Adhesives can be crosslinked to give high shear strengths, such as by radiation and/or a chemical crosslinking agent. Such adhesives can potentially have high shear strength provide low debonding force and can easily be removed when stretched.

In some embodiments, the pressure-sensitive adhesive comprises or consists essentially of a pure rubbery copolymer of an acrylic polymer, such as isooctyl acrylate, 2-ethyl hexyl acrylate, isononyl acrylate, decyl acrylate, dodecyl acrylate, butyl acrylate, hexyl acrylate, mixtures thereof, and the like (between about 50% and about 98%, between about 70% to about 98%, between about 80% to about 97%, between about 90% and about 96%, between about 92% and about 96%, or about 94% by weight and acrylic acid (between about 2% and about 50%, between about 2% and about 30%, between about 3% and about 20%, between about 4% and about 10%, between about 4% and about 8%, or about 4%, and overlapping ranges thereof). In some embodiments, the adhesive comprises or consists essentially of a 2-ethylhexyl acrylate-vinyl acetate copolymer or a blend of this copolymer with 2-ethylhexyl acrylate-n-test-butyl acrylamide copolymer, the mixture cross-linked, or cured, with a suitable catalyst, e.g., Zirco dryer, a zirconium organic complex catalyst.

The adhesive layer could also comprise, or consist essentially of, blends of (i) polydiorganosiloxanes (e.g., those having an average molecular weight from about 5,000 to about 10,000,000, such as from about 50,000 to about 1,000,000) with (ii) copolymeric silicone resins (also referred to as an "MQ resin" typically having an average molecular weight of from about 100 to about 1,000,000, such as from about 500 to about 50,000 average molecular weight) comprising triorganosiloxy units and $SiO_{4/2}$ units. In some embodiments, the ratio by weight of polydiorganosiloxane to copolymeric silicone resin is about equal to, or more than about 1:1, 1.05:1, 1.1:1, 1.2:1, 1.3:1, 1.4:1, 1.5:1, 1.6:1, 1.7:1, 1.8:1, 1.9:1, 2:1, 3:1, 4:1, 5:1, 7:1, 8:1, 10:1, or more. In some embodiments, the ratio by weight of polydiorganosiloxane to copolymeric silicone resin is about equal to, or less than about 1:1, 0.95:1, 0.9:1, 0.8:1, 0.7:1, 0.6:1, 0.5:1, 0.4:1, 0.3:1, 0.2:1, 0.1:1, or less. In other embodiments, the adhesive layer does not comprise a silicone adhesive.

It is beneficial in some cases, in terms of improving PSA properties, to provide a chemical mechanism of reacting the copolymeric silicone resin with the polydiorganosiloxane. To achieve such a reaction, two different reaction chemistries have been commonly used; condensation chemistry and addition-cure chemistry. Silicone PSAs based on condensation chemistry can be prepared by admixing silanol functional copolymeric silicone resins comprising triorganosiloxy units and $SiO_{4/2}$ units with silanol-endblocked polydiorganosiloxanes. Such blends, which are usually a solvent solution of copolymeric silicone resin and polydiorganosiloxane, can be generally applied to a backing, heated to remove solvent, and crosslinked, if necessary, to improve the physical properties of the PSA. The copolymeric silicone resin and the polydiorganosiloxane are intercondensed, providing intra- and inter-condensation within the adhesive. According to these references the condensation between the copolymeric silicone resin and the polydiorganosiloxane can be effected either in the presence of catalyst at ambient or elevated temperature, or in the absence of catalyst at elevated temperatures, as well as prior to application of the PSA to a backing, or subsequent to application of the PSA to a backing. Effective catalysts for promoting the silanol condensation reaction include organometallic compounds and metal salts of carboxylic acids. An additional method of intercondensing silicone resins and polydiorganosiloxanes is through the addition of orthosilicates and polysilicates.

A silicone PSA comprising the intercondensation product of a silanol functional polydiorganosiloxane and a silanol functional copolymeric silicone resin, as discussed above, can optionally include a free radical polymerization catalyst, such as a diaryl peroxide crosslinker, to crosslink the adhesive composition, thereby improving the high temperature shear properties of the PSA with only a slight loss in peel adhesion.

The polydiorganosiloxanes used in the preparation of the silicone PSA component of can include, for example, polydimethylsiloxane polymers and poly(dimethylsiloxane/diphenylsiloxane) copolymers. Copolymeric silicone resins can include copolymeric silicone resins having one or more of the following functionalities: silicon-bonded hydrogen, silicon-bonded alkenyl, and silanol. Other useful silicone resins include three component terpolymers comprising $R_3SiO_{1/2}$, $SiO_{4/2}$, and $R_2SiO_{2/2}$ structural units (MQD resins) where R is selected from the group consisting of alkyl radicals comprising 1 to 3 carbon atoms and phenyl radical, wherein the ratio of $R_3SiO_{1/2}$ units to $SiO_2$ is between about 0.5 and about 1.0, such as between about 0.6 and about 0.9, or between about 0.7 and about 0.8.

Silicone PSAs prepared by addition-cure chemistry generally comprise polydiorganosiloxanes having alkenyl groups, copolymeric silicone resins comprising $SiO_{4/2}$ and $R_3SiO_{1/2}$ structural units wherein R is as defined previously having one or more of the following functionalities: silicone-bonded hydrogen, silicone bonded alkenyl groups such as those selected from the group consisting of vinyl, allyl, and propenyl; or silanol, optionally a crosslinking or chain extending agent, and platinum or other noble metal hydrosilation catalyst to effect the curing of the silicone PSA.

In some embodiments, the adhesive layer can comprise of bioadhesives (BAs). BAs in some cases exhibit good tack when adhered to hydrated biological substrates/issues. Non-limiting examples includes slightly cross-linked polyacrylic and polymethacrylic acids as well as blends of hydrophilic cellulose derivatives (40-95%) with polyethylene glycol. In ether embodiments, the adhesive layer can comprise different combinations of PSA and BA polymeric materials of different hydrophilicity and thus different solubilities in water or in the liquids secreted by the tissue region in contact with the adhesive layer. Hydrogels and hydrocolloids can also be formulated to provide a more gentle adhesive. Gel adhesives provide an alternative to pressure-sensitive adhesives and can be gentle to the skin. A gel adhesive has a low peel with skin and can be removed with little damage and it typically wets out the surface well. Common gel adhesives include, but are not limited to, silicone and polyurethane gels. Gel adhesives can also be utilized to temporarily obstruct the urethra and assist with urinary retention in some embodiments.

In some embodiments, adhesive inactivation can be utilized to effect pain-free removal. Acrylic, polyurethane or rubber-based adhesives for example may be used in conjunction with the deactivation method. The deactivatahle adhesive can form strong bonds until it is time for removal. Using a trigger mechanism, at the time where removal is desired, the adhesive is made to lose its bond strength. Various trigger mechanisms, such as a light source, use of liquid solution such as water or saline, or solvents such as dipropylene glycol methyl ether, isoparaffin C10-C11, or isopropyl alcohol. The use of microcapsules filled with oils can be utilized. Such substances could be present in a rupturable reservoir on the device or other location when removal is desired. Some examples include plant extracts, petroleum extracts, and animal extracts. Plant extracts could include olive oil, safflower oil, cotton seed oil, peanut oil, soybean oil, castor oil, sesame oil, aloe vera and eucalyptus oil. Animal extracts could include fatty acids such as those found in emu oil. Petroleum extracts could include petrolatum (petroleum jelly) and mineral oil. One example of petrolatum is white petrolatum USP skin protectant, which is a semi-solid mixture of hydrocarbons that is capable of breaking down certain adhesives, such as cyanoacrylates. Any of the aforementioned components or combinations thereof may serve as a lubricant, in addition to or instead of for adhesive inactivation. In some embodiments, the device, or adhesive layer of the device, does not comprise a lubricant.

In some embodiments, the adhesive (or a portion of, or the entire device) can be biodegradable and/or bioabsorbable, initially having a very high bond strength that degrades relatively quickly over time, and may naturally dissolve and/or fall off the skin within a desired time period, such as within about 24 hours, 18 hours, 12 hours, 10 hours, 8 hours, 6 hours, 5 hours, 4 hours, 3 hours, 2 hours, or even less. One advantageous example is an adhesive that can be sprayed onto or otherwise applied to the anatomic region of interest, e.g., a clitoral structure without necessarily requiring additional patch layers as described above. Such an embodiment could also be advantageous for convenience and cleanliness purposes in that a patient would not have to directly touch their anatomy. In some embodiments, the adhesive (such as a gel, for example) can be contained within an applicator, such as a spray can or tube with a movable wall similar to a tube of toothpaste for example. The applicator can include an actuator (e.g., a lever, button, or trigger for example) configured such that the applicator dispenses a repeatably consistent volume of adhesive sufficient to apply the desired mechanical stimulus to the clitoral structure each time the applicator is actuated.

In some embodiments, the device, including the adhesive layer, is water or otherwise liquid-resistant. This can be beneficial, in some cases, for a patient active in water sports, such as swimming, and/or to prevent or reduce the likelihood of premature detachment such as during urination. In some embodiments, the adhesive and/or device could be biodegradable characteristics such as the above such that the adhesive and/or device is flushable, e.g., in a toilet without risk of clogging such that it is discreetly and conveniently disposable, and safe for sewers and septic systems. In some embodiments, the device is not biodegradable or bioabsorbable. In some embodiments, about or less than about 20%, 15%, 10%, 5% of the total mass of the device comprises non-biodegradable materials.

Biodegradable adhesives could include, for example one or more biodegradable polymers, which could include natural biodegradable polymers, e.g., collagen, atelocollagen, alkali-solubilized collagen, gelatin, keratin, albumin, globulin, fibrinogen, glycosaminoglycan, chitin and chitosan, and derivatives thereof, and/or synthetic biodegradable polymers including polyamino acid and polyalcohol, and derivatives thereof. The solvent for dissolving the biodegradable polymer may be, for example, distilled water, buffer solution and/or an organic solvent. The organic solvent could include dimethylsulfoxide (DMSO), N,N-dimethylformamide (DMF), lactic acid, lactic acid oligomer, polyethylene glycol and/or polypropylene glycol.

In some embodiments, an adhesive could include one or more of: one, two, or more polymeric, elastomeric microspheres wherein the microspheres are the reaction product of polymerizable starting materials comprising at least one $C_4$-$C_{14}$ alkyl (meth)acrylate monomer and optionally at least one comonomer; an initiator for the polymerizable monomer starting materials present in amounts ranging from 0.1 to approximately 2 parts per weight per 100 parts by weight of the polymerizable monomer starting materials; a polymeric stabilizer in an amount of between about 0.1 parts and about 3 parts by weight per 100 parts by weight of the microspheres; a surfactant in an amount of no greater than about 10 parts, 5 parts, 3 parts, 2 parts, or less by weight per 100 parts by weight of the microspheres; and a chain transfer agent in an amount sufficient to produce 20-99%, or 30-98% of a heptane soluble portion in the microspheres.

In some embodiments, the adhesive can either be directly coated onto the backing layer, or it can be formed as a separate layer and then later laminated to the backing. The adhesive may be applied to the backing layer by various techniques, including, for example, transfer techniques, spray techniques, screen printing, slot die coating, the use of a "kiss" roll, or reverse roll coating and the like. The adhesive mass in some cases can be firmly bonded to the backing layer, and primer is optionally used.

In certain transfer techniques, the adhesive mass may be cast from a solvent on a release layer having a heat-resistant, insoluble anti-stick surface, e.g. a silicone release coated carrier. It is passed through an oven to remove the solvent and, if necessary, to blow and cure the mass. The backing layer can then be laminated to the mass by being pressed down thereon at the end of the oven line, the release layer ultimately being stripped away. When applying the adhesive mass by spraying, the volatiles therein are flashed and the mass is disposed on the backing layer in a stringy pattern. The stringy mass is anchored during the subsequent oven treatment, resulting in a highly breathable coating.

In some cases, in order to improve adhesion of the adhesive layer to the backing, the backing can be pretreated prior to the coating step or the laminating step in one or more of the following ways: corona discharge, plasma discharge, flame treatment, electron beam irradiation, ultraviolet radiation, acid etching, or chemical priming. Such pretreatments can be carried out with or without reactive chemical adhesion promoters such as hydroxyethyl acrylate or hydroxyethyl methacrylate, or other reactive species of low molecular weight.

The adhesive layer, in some embodiments, can also include additives such as tackifiers, plasticizers, anti-oxidants, processing oils, stabilizing agents for enhanced shelf-life, and the like. Agents added to stabilize the adhesive against the detrimental effects of gamma sterilization include, but are not limited to, those commercially available as Irganox 1010, Irganox 1076, Irganox 245, Irganox 3052F, Irganox E201, Irganox B225, Ubiquinone, Tinuvin 662, and Tinuvin 770.

In some embodiments, the adhesive layer further include a tackifier and/or plasticizer. The plasticizer is selected for its biocompatibility and its ability to modify the compliance of the adhesive formulation and to achieve the other properties described herein. The plasticizer can be non-volatile and be insoluble in water and in some cases should also not absorb water or other bodily fluids. The adhesive layer can be in some cases about 5% by weight to about 70% by weight plasticizer, and in some cases may be in the range of about 15% by weight to about 60% by weight plasticizer. In some embodiments, the plasticizer may be present in the range of about 25% to about 50% by weight, or about 30% to about 40% by weight.

Some examples of plasticizers that can be used include triisodecyl trimellitate; tributyl trimellitate; tri-n-hexyl trimellitate; tris n-(C7-11)alkyl ester branched and linear 1,2,4 benzenetricarboxylic acid; butyl benzoate; di-ethylhexylphthalate; di-octylphthalate; di-butylphthalate; diethylhexyl adipate; dibutyl adipate; triethyl citrate; tributyl citrate; acetyl triethyl citrate; acetyl tri-butyl citrate; n-butyryl tri-n-hexyl citrate; triacetin; glycerin; caprylic/capric triglyceride; tricaprin; tricaprylin; propylene glycol dicaprate; propylene glycol dicaprylate/dicaprate; poly(ethylene glycol) (PEG); hydrogenated vegetable oil; hydrogenated seed oil; PEG dilaurate; PEG diethylhexylonate; and combinations thereof.

Some adhesive layers further may include up to about 5%, 10%, 20%, 30%, 40%, 50%, or more by weight of a tackifier. The tackifier may be selected from the group consisting of rosin esters, polymerized rosins, hydrogenated rosins, polyterpenes, styrenated terpenes, polymerized hydrocarbon resins, alpha methyl styrenes, alpha methyl styrene phenolics and combinations thereof. Some specific tackifiers include those commercially available as Escorez 1310, Sylvares SA120, Sylvares TP105, Foral 85, and Sylvares 540. As with the plasticizer, the tackifier is selected for its biocompatibility (i.e., its ability to be safely in contact with the skin and/or bodily fluids) and compatibility with (i.e., its ability to form a single phase with) the adhesive.

In some embodiments, the weight of the dry adhesive layer per surface area of backing layer of which the adhesive is applied to may be in the range of about 7 g/m$^2$ to about 100 g/m$^2$, between about 14 g/m$^2$ to about 55 g/m$^2$, between about 20 g/m$^2$ to about 80 g/m$^2$, between about 20 g/m$^2$ to about 40 g/m2, between about 40 g/m$^2$ to about 60 g/m$^2$, between about 60 g/m$^2$ to about 80 g/m$^2$, between about 80 g/m$^2$ to about 100 g/m$^2$, or overlapping ranges thereof.

Regardless of the adhesive composition used, the final adhesive layer can in some embodiments can be pressure sensitive, hydrophilic and non-allergenic (e.g., latex-free in some embodiments).

In some embodiments, the thickness of the adhesive layer can range from about 25 micrometers to about 1,000 micrometers, between about 25 micrometers and about 50 micrometers, between about 50 micrometers and about 400 micrometers, between about 50 micrometers and about 200 micrometers, between about 100 micrometers and about 200 micrometers (e.g., about 150 micrometers), or between about 100 micrometers and about 300 micrometers. In some embodiments, the thickness of the adhesive layer is between about 0.002" and about 0.010", between about 0.004" and about 0.008", between about 0.005" and about 0.007", or about 0.006".

In some embodiments, the device such as a patch for example could include a fragrance-emitting element configured to provide a pleasing olfactory scent, such as a perfume composition or a polyethylene bead, for example. In some embodiments, the device could be completely or partially transparent, or in various skin tones to blend in with the surrounding anatomy. In other embodiments, the device could have a color or other visual or tactile indicia (e.g., a phosphorescent material that illuminates in the absence of light) that contrasts with the surrounding anatomy, to assist with placement and/or removal.

Figure 5:
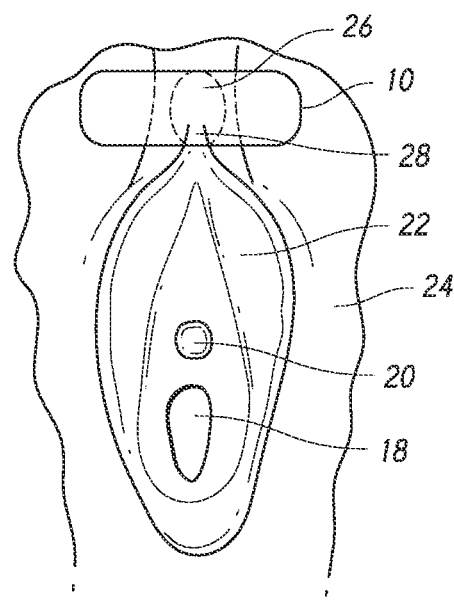
FIG. 5 is a sketch of a vagina illustrating components relevant to the invention and showing application of the patch to the clitoral hood.

The patch 10 or other device can be applied with the adhesive layer directly on the clitoral region or other anatomical structures as shown. FIG. 5 is a sketch of a vagina illustrating certain components of a vagina, including the vaginal opening 18, the urethral opening 20, the labia majora 22, the labia majora 24, the clitoral hood 26 and the clitoris at 28. In this embodiment, the patch 10 is applied solely to the clitoral region by being applied to the clitoral hood 26. Not to be limited by theory, the adhesive layer 14 physically stimulates the clitoral nerves to provide an inhibitory effect on the bladder, relieving urinary urgency and frequency. In some embodiments, the device, e.g., patch preferentially exerts pressure, traction, friction, vibration, or other stimulus on one or more clitoral structures. In some embodiments, the device e.g., patch exclusively exerts a mechanical stimulus on one or more clitoral structures, but not to any adjacent anatomical structures, such as the labia majora, labia minora, urethra, vagina, or mons pubis, for example. In some embodiments, the device, e.g., patch exerts a force on a clitoral structure that is about or at least about 10%, 25%, 50%, 100%, 150%, 200%, 250%, 300%, 400%, 500%, or more relative to an adjacent non-clitoral anatomical structure, such as any non-clitoral anatomical structure disclosed herein.

Figure 5A:
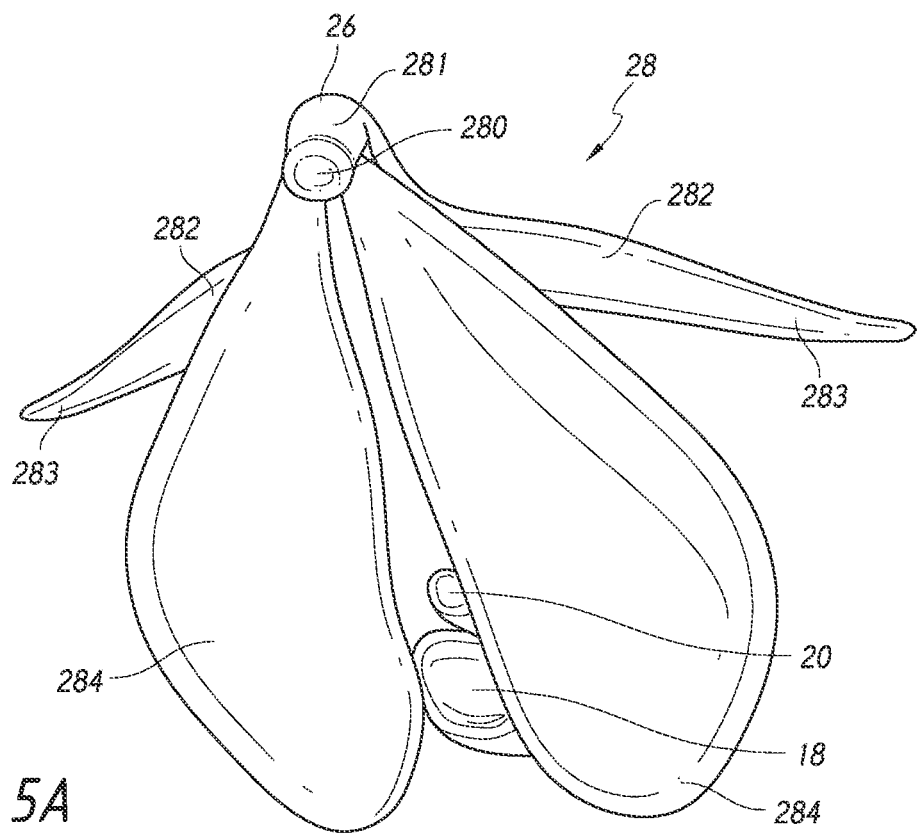
FIG. 5A is a sketch illustrating internal and external clitoral anatomy.

FIG. 5A schematically illustrates certain parts of both internal and external female anatomy in greater detail. The clitoris 28 is a complex structure, and includes both external and internal components. The clitoris 28 includes the non-erectile glans 280, the clitoral body or shaft 281 (being both internal and external), and the clitoral hood or prepuce 26 externally. Internally, the clitoris includes two erectile bodies known as the corpora cavernosa 282, two clitoral crura 283 and the vestibular or clitoral bulbs 284. Also shown are the vaginal opening 18 and the urethral opening 20. Research has indicated that the clitoral tissue also extends internally into the anterior wall of the vagina, and may include the Grafenberg ("G") spot (not shown), reportedly located between about 1 and about 3 inches up the anterior vaginal wall between the vaginal opening 18 and the urethra 20. The clitoral glans 280 typically has a width of between about 0.098 inches and about 0.177 inches, and the total clitoral length including glans 280 and body 281 is typically between about 0.63 inches±about 0.17 inches. The components of devices, e.g., an adhesive layer configured to exert mechanical stimulus, e.g., pressure on a clitoral structure could have a length or width that matches that of the aforementioned anatomical structures, or within about 50%, 40%, 30%, 20%, 15%, 10%, 5%, or less of that of the clitoral structure.

Not to be limited by theory, clitoral innervation and perineal neurovascular bundles are paired terminations of the pudendal neurovascular bundles. The clitoral neurovascular bundle ascends along the periosteum of the ischiopubic ramus to meet the neurovascular bundle from the other side close to the midline. Where the crura united to become the body of the clitoris, the clitoral neurovascular bundles pass to the superior surface of the clitoral body. After some minimal branching the dorsal clitoral nerves pass largely as intact, large neural trunks into the clitoral glans. The perineal neurovascular bundle supplies the urethra and bulbs. The cavernous or autonomic neural anatomy is often microscopic, and supplies the female urethral sphincter complex and clitoris. The branches of the cavernous nerve were noted to join the clitoral dorsal nerve at the hilum of the clitoral bodies. The cavernous nerves originate from the vaginal plexus component of the pelvic plexus, and travel generally at the 2 and 10 o'clock positions along the anterior vaginal wall, and then at the 5 and 7 o'clock positions along the urethra. Physical stimulus, e.g., pressure can be applied to any one, two, or more of the aforementioned components of the clitoris in order to provide neuromodulation of any of the nerves mentioned herein to treat or prevent pelvic conditions, including but not limited to urinary incontinence. To provide neuromodulation to nerves innervating internal clitoral structures, a device could be inserted, for example, intravaginally to apply mechanical stimulus, e.g., pressure to the anterior vaginal wall, and thus also applying stimulus to the corpora cavernosa, clitoral crura, and the vestibular or clitoral bulbs proximate to the anterior vaginal wall. The device could take the form of a tampon or stent-like structure configured to exert mechanical stimulus, e.g., pressure on the anterior vaginal wall, or a vaginal extension of a intra-uterine device, for example.

Not to be limited by theory, there is evidence that the clitoris with its hood has neural pathways to the parasympathetic visceral efferent and afferent fibers that arise from the sacral center (S2-S4), and possibly also the sympathetic preganglionic afferent and visceral efferent fibers from the thorocolumbar center (T10-T12 and/or T11-L2), which can help to explain the beneficial effect on the bladder, urethra and other civic structures such as the colon, which have similar innervations. The parasympathetic nervous system (PNS), through its effect on cholinergic receptors in the bladder and urethra, excite the detrusor muscle and inhibit urethral smooth muscles to promote voiding. The Preganglionic Sympathetic nerves from T10 to T12 com are the conduit for postganglionic neurons to travel in the hypogastric nerve and synapse in the adrenergic ganglia in the pelvic plexus. The sympathetic nervous system (SNS) via its effect cm beta-adrenergic receptors inhibits the detrusor muscle and stimulates urethral smooth muscle via alpha-adrenergic receptors, thus promoting continence.

Figure 5B:
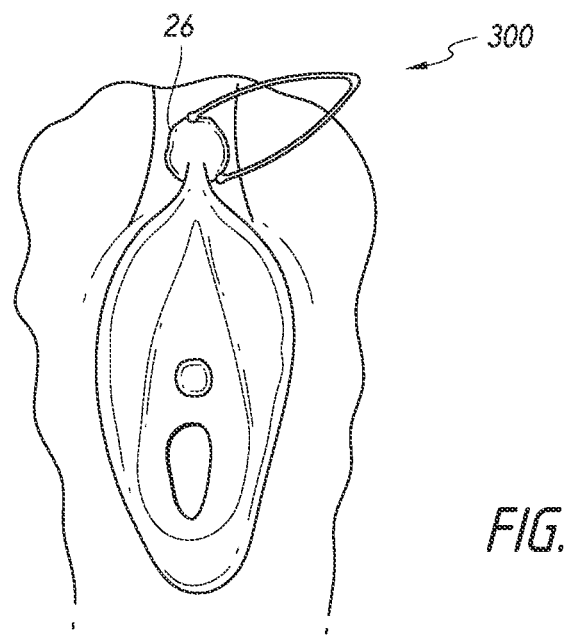
FIG. 5B illustrates an embodiment of a soft clamp applying a stimulus, e.g., mechanical pressure to the clitoral hood.

FIG. 5B illustrates schematically an embodiment of a clamp 300, such as a small clothespin-like device with a fulcrum and a plurality of lever arms, configured to exert mechanical stimulus, e.g., pressure to a region of the clitoris, such as the clitoral hood 26 as shown, but not sufficient pressure to cause substantial discomfort to the patient. In some embodiments, a ring or band could be used instead of or in addition to the clamp 300. The clamping force, in some embodiments, could be about or less than about 300 mm Hg, 250 mm Hg, 200 mm Hg, 150 mm Hg, 125 mm Hg, 100 mm Hg, 80 mm Hg, 60 mm Hg, 40 mm Hg, 30 mm Hg, 20 mm Hg, 10 mm Hg, or even less.

Figure 5C:
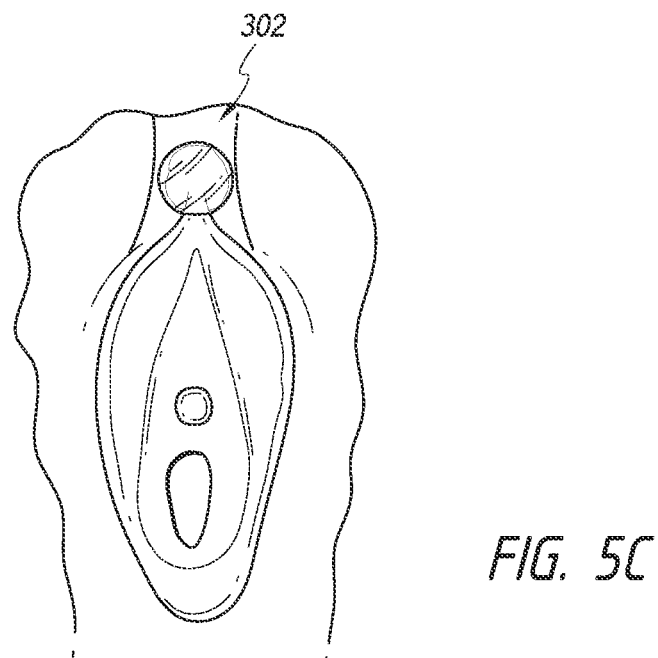
FIG. 5C illustrates an embodiment of a suction cup applying a stimulus, e.g., mechanical pressure to the clitoral hood.

FIG. 5C illustrates schematically an embodiment of a suction cup 302 configured to create a vacuum sufficient to exert mechanical stimulus, e.g., pressure to a region of the clitoris, such as the clitoral hood 26 as shown, but not sufficient pressure to cause significant discomfort to the patient. In some embodiments, the vacuum pressure is sufficient to maintain a seal on the desired clitoral structure, and can be about or less than about negative 300 mm Hg, 250 mm Hg, 200 mm Hg, 150 mm Hg, 125 mm Hg, 100 mm Hg, 80 mm Hg, 60 mm Hg, 40 mm Hg, 30 mm Hg, 20 mm Hg, 10 mm Hg, or even less.

Figure 6:
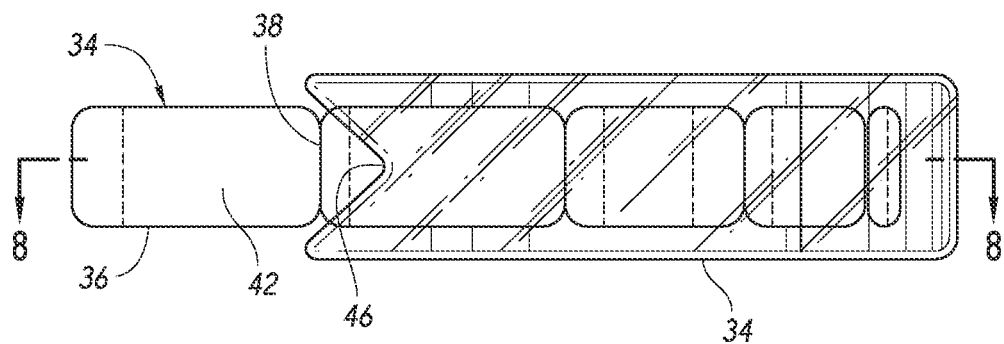
FIG. 6 is a top view of a transparent dispenser showing a plurality of patches arranged linearly and connected by tear lines.
Figure 7:
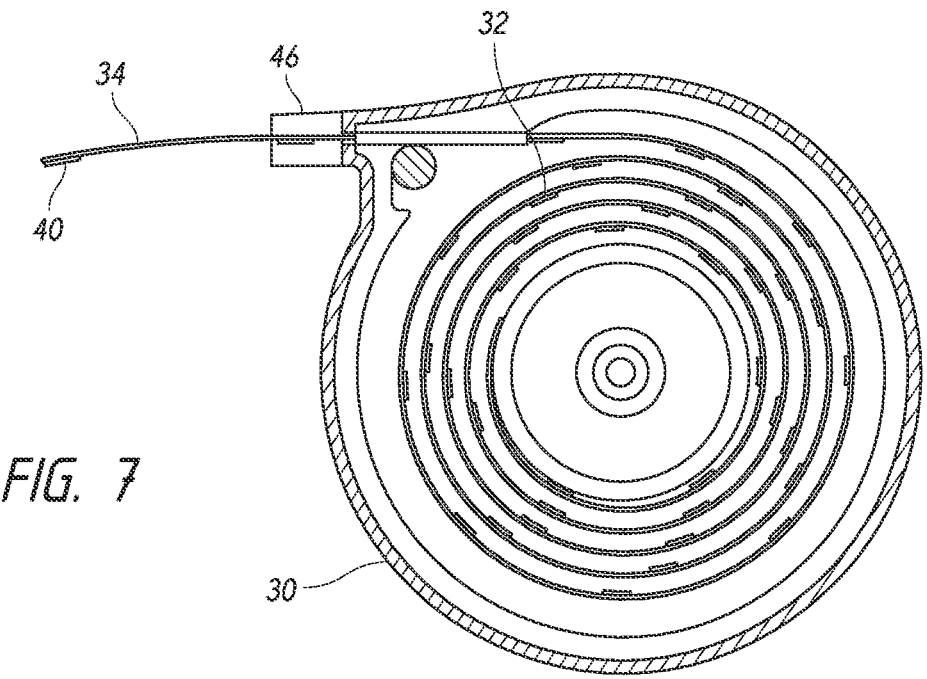
FIG. 7 is a cross-sectional view of the dispenser of FIG. 7.
Figure 8:
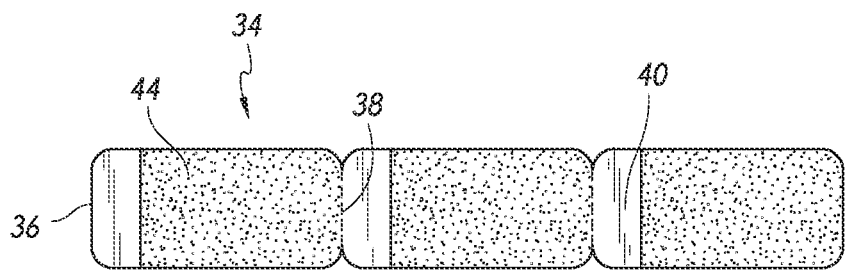
FIG. 8 shows the underside of three of the plurality of patches contained in the dispenser of FIG. 7, connected by tear lines.
Figure 9:
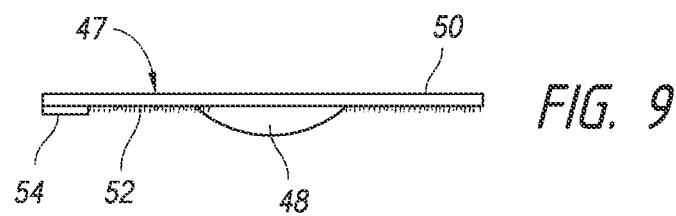
FIG. 9 shows a patch to which a solid, curvilinear object is secured to the front side of a backing sheet having an adhesive layer on said front side.

While a single patch 10 is shown in FIG. 1, in actual production and/or sale, a plurality of such patches may be packaged as a kit. In some embodiments, the patches can be formed or placed on a single release sheet and packaged as a kit whereby individual patches can be removed and applied as needed. FIGS. 6, 7 and 8 show an embodiment in which a dispenser 30 is provided containing a roll 32 of a linearly arranged array 34 of patches 36. Each roll 32 could include any number of patches, such as about or at least about 5, 10, 20, 30, 40, 50, 100, or more patches 36. Referring specifically to FIG. 8, the undersides of three patches 36 of the linear patch array 34 are shown. The patches 36 are connected by tear lines 38 and have a paper or cloth tab 40 on each end. Each patch has a backing sheet 42 (FIG. 7) and an adhesive layer 44 (FIG. 9). The tab 40 is secured to the underside of the patch by the adhesive layer 44. The dispenser 30 could be placed in a housing, such as a compact case. The case could also include a mirror to assist the patient in placing the device, as well as hand wipes or an antibacterial gel for hygienic purposes. In some embodiments, the kit could include any combination of a plurality of patches, a housing, a mirror, instructions for placing the patches on a clitoral structure, and a dispenser configured to individually dispense a patch. The patches can be placed on a release layer in a rolled configuration, and separated by perforations as previously described.

In operation, one grasps the tab end of a patch extending from the mouth 46 of the dispenser having a slot, pulling it until the tab 40 of the next patch is momentarily stopped by the closeness of the dispenser mouth 46. The withdrawn patch is then detached from the array along its tear line 38.

Referring to FIG. 9, a patch 47 is shown in which a solid but pliable curvilinear object 48 is secured to the underside of a backing sheet 50 having an adhesive layer 52 on the patch underside which carries the solid object 48 as well as a paper or cloth tab 54. The device of FIG. 9 can be carried as a linear array, separated by tear lines in the manner of the patches 35 of FIGS. 6-8 by the dispenser 30. A separated patch is applied directly to the clitoral region, over the hood, to apply physical pressure on the clitoral region. Other shapes for the solid object can be provided, such as a spherical shape, or the like.

Figure 10:
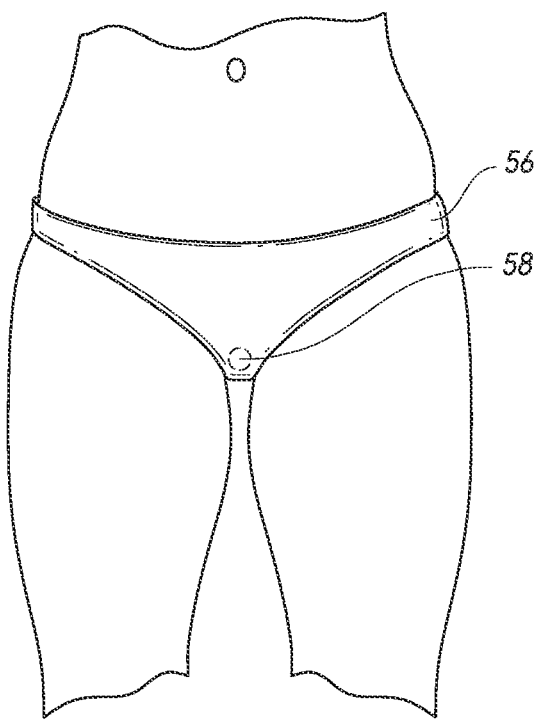
FIG. 10 shows a supportive garment, in this case a panty, having a solid object mounted therein so as to be applied to the clitoral region to apply a stimulus, e.g., physical pressure thereon.
Figure 11:
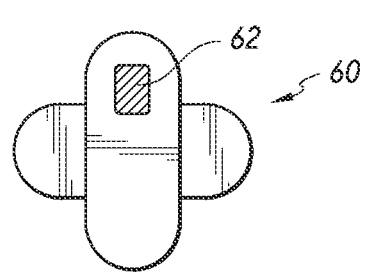
FIG. 11 illustrates an embodiment of a sanitary napkin coupled to a device configured to apply a stimulus, e.g., mechanical pressure to a clitoral structure.

Referring to FIG. 10, a panty 56 or other undergarment is shown having a solid object 58, which can be the solid object 48 of FIG. 9, mounted therein, such as by adhesive or sewing, so as to be applied to the clitoral region, such as over the hood, to apply physical pressure thereon. In some embodiments, as illustrated in FIG. 11, a solid object or a patch 62 as described and illustrated herein could also be operably attached to a sanitary napkin 60, such as a menstrual pad, tampon, or diaper for example, and configured to apply physical pressure to the clitoral region. In some embodiments, the solid object can be a soft molded component and does not necessarily require an adhesive layer, and can simply slide between the labia and provide contact to the clitoris. Such an object can be held in place by the labia as well as an undergarment of the patient, for example.

In some embodiments, devices as disclosed herein can be configured for application of mechanical pressure to the clitoris, such as patches for example, can be used synergistically in combination with a urethral insert (e.g., a plug) for the treatment or prevention of a condition, such as incontinence for example. Non-limiting examples of a female urethral insert are described in U.S. Pat. No. 5,090,424 to Simon et al., which is hereby incorporated by reference in its entirety. Another example is the FemSoft® Insert from Rochester Medical Corp, (Stewartville, Minn.).

Figure 12A:
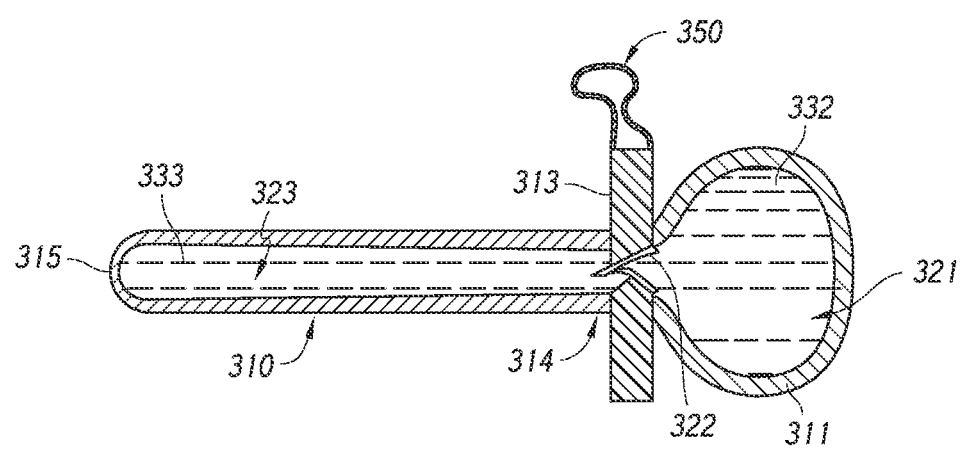
FIG. 12A illustrates an embodiment of a urethral plug having a clitoral extension segment.

In some embodiments, a modified urethral insert is operably connected to a device configured to physically press against the clitoral region. FIG. 12A illustrates one embodiment of a modified urethral plug 310 with a clitoral component. A bellows 311 defines cavity 321, and is used to transport fluid 332 contained in cavity 321 through a check valve 322 which is located within metal plate 313. Extending from the plate 313 is a clitoral extension segment 350 configured to physically press against the clitoral region. The clitoral extension segment 350 can in some embodiments be biased toward the body as shown to more optimally press against a clitoral structure. In some embodiments, the clitoral extension segment 350 includes a patch having an adhesive layer 352 (that can be as described above with respect to the patch embodiments) to better reversibly attach and apply consistent pressure to the clitoral region. The clitoral extension segment 350 could also include a suction cup, clamp, or other element as described elsewhere herein for applying physical pressure to the clitoral region. In some embodiments, clitoral extension segment 350 can extend from the bellows 311 or the shaft of the shaft of the plug 310 rather than from the plate 313.

The bellows 311 can be made from a material which makes it conformable to the body and comfortable for the patient when the urethral plug is in place. The fluid 332 is transported to cavity 323 located within plug 310 becoming fluid 333. The wall of the plug 310 can be relatively constant in outer diameter allowing the device to be easily inserted. However, the wall thickness varies from the metal plate 313, beginning at location 314 to the proximal end 315 where the wall is thinnest, allowing the greatest inflation. The fluid 332 can be any fluid which can be pumped from cavity 321 to cavity 323 through check valve 322.

Figure 12B:
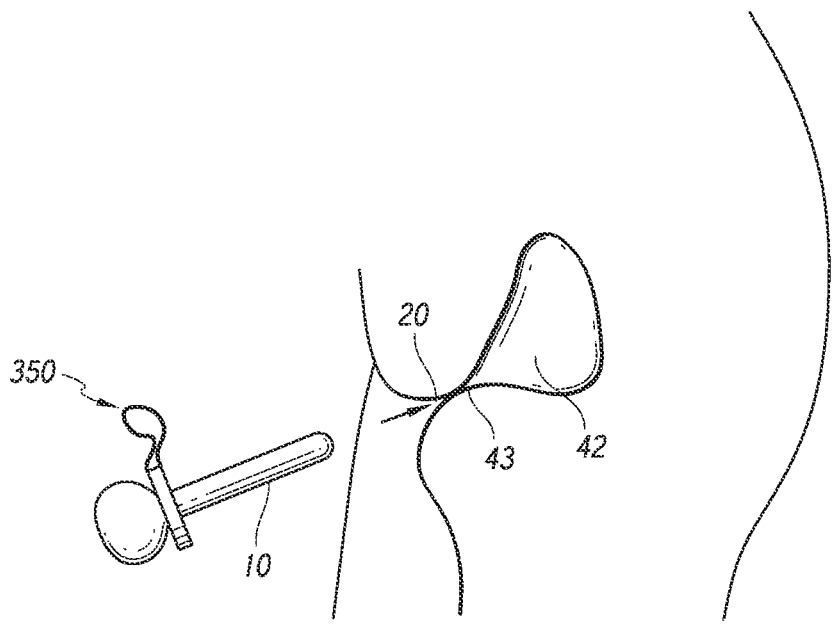
FIGS. 12B-12C illustrate a method of deploying a urethral plug having a clitoral extension segment.
Figure 12C:
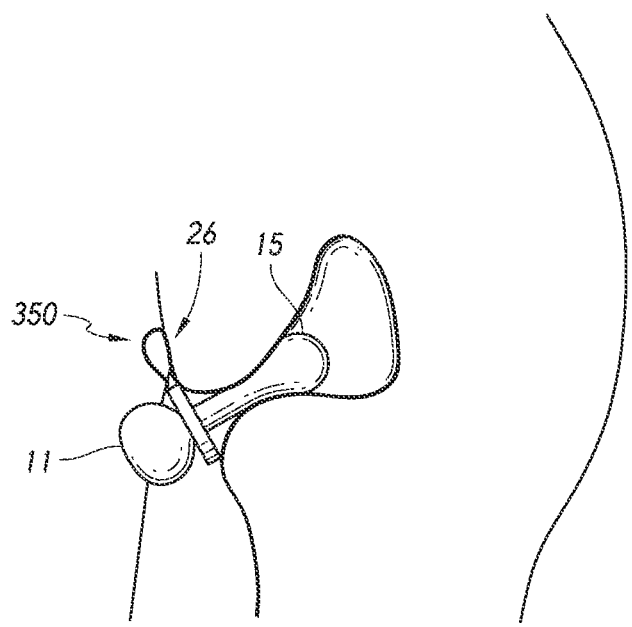

As shown in FIG. 12B, the deflated urethral plug 310 is inserted into the patient's urethra 20. After insertion, as shown in FIG. 12C, bellows 311 is pumped by the patient so that the distal end preferentially expands into space 342 beyond sphincter 343 and/or into the bladder neck or bladder thus causing the device 310 to assist in sealing the urethra 20, while the clitoral extension segment 350 applies physical pressure to the clitoral region, such as the clitoral hood 26. For removal, bellows 311 is gently tugged on by the patient so that the expanded proximal end 315 deflates, thereby allowing urethral plug 310 to be easily removed from the urethra 20, and the clitoral extension segment 350 can decouple from the clitoral structures as described elsewhere herein.

The devices, e.g., patches as described herein enable the neuromodulation, e.g., stimulation of the visceral pelvic or somatic nerves or their pathways of a female person suffering from a pelvic condition of nerve dysfunction. Systems and methods as described herein can apply a non-electrical, external physical-mechanical stimulation to, for example, the clitoral region. As discussed elsewhere herein and not to be limited by theory, such physical stimulation can result in neuromodulation. Conditions that can be treated or prevented can include, but are not limited to female urinary frequency or urgency, overactive bladder, stress, urge, or mixed urinary incontinence, fecal incontinence including retention fecal incontinence, constipation, interstitial cystitis, or pelvic pain, such as vulvodynia, or endometriosis. In some embodiments, systems and methods as disclosed herein can result in neuromodulation of the pudendal nerve, cavernous nerve, sacral nerve, and branches thereof (including, for example, the inferior rectal nerve, the perineal nerve, the dorsal nerve of the clitoris, and/or the posterior labial nerves), and affect the external urinary sphincter muscle, the internal urinary sphincter muscle, the detrusor muscle, the external anal sphincter muscle, the internal anal sphincter muscle, or others. In some embodiments, devices as disclosed herein can be configured to exert a mechanical force sufficient to result in neuromodulation to treat a condition such as, for example, incontinence or others as listed above while at the same time not causing or substantially causing female sexual arousal, manifested as, for example, psychological arousal, clitoral engorgement, vaginal lubrication, and/or nipple erection.

The devices as disclosed herein can be applied at desired time intervals depending on the desired clinical result. For example, a patient may apply a device, e.g., a disposable patch, to the desired anatomical region daily, twice daily, three times a day for example, and after a shower or bath. In some embodiments, the device is applied to the desired anatomical region for about or no more than about 72 hours, 48 hours, 24 hours, 18 hours, 12 hours, 10 hours, 8 hours, 6 hours, 4 hours, 3 hours, or 2 hours a day. In some embodiments, the device is applied during periods of strenuous physical activity, normal daily activity, and/or during sleep.

The following examples further illustrate non-limiting embodiments of the invention.

EXAMPLE 1

A patient suffering from female urinary incontinence can be given a dispenser of FIG. 6 with instructions to tear a section containing a patch along the line of weakness (e.g., perforation line) and apply it over the clitoral hood to treat or prevent urinary incontinence. For as long as the incontinence continues, a new patch should be applied each day and after each shower or bath. The patch will serve to stimulate the visceral pelvic or somatic nerves or their pathways pelvic to treat nerve dysfunction. No adverse side effects would be suffered.

EXAMPLE 2

The procedure of Example 1 can be followed to provide relief from any of the following conditions: urinary frequency or urgency, overactive bladder, urinary retention, fecal incontinence, constipation, interstitial cystitis, or vulvodynia to stimulate the visceral pelvic or somatic nerves or their pathways pelvic to treat nerve dysfunction. No adverse side effects would be suffered.

EXAMPLE 3

A patient suffering from female urinary frequency or urgency, overactive bladder, urinary incontinence or retention, fecal incontinence, constipation, interstitial cystitis, or vulvodynia can be given a patch such as shown in FIGS. 6-8 with instructions to apply it over the clitoral glans, shaft, and/or hood. For as long as the incontinence continues, a new device may be applied each day and after each shower or bath. In some embodiments, the device is waterproof and will remain adhered after bathing. The device, in some embodiments, will serve to stimulate the visceral pelvic or somatic nerves or their pathways to treat nerve dysfunction. No adverse side effects would be suffered.

EXAMPLE 4

In one embodiment, a subject identified as having a pelvic disorder such as stress urinary incontinence) will obtain a device (e.g., without professional intervention) for application to the pelvic area (e.g., one or more clitoral structures), wherein the device includes one or more (or all) of the following features:

(i) an adhesive,
(ii) the adhesive may form one, two, or more layers and configured for application at least between opposing folds of the labia majora, and may span the labia or be sized to be placed exclusively between the labia;
(iii) the adhesive may be configured such that when removed from the clitoral structures less than about 50%, 40%, 30%, 20%, 10%, or less of the adhesive surface area is covered by detached skin cells of the patient;
(iv) the device, or the adhesive can be configured to decouple from the patient's clitoral structures within about 24 hours, 18 hours, 12 hours, 10 hours, 8 hours, 6 hours, or less;
(v) the device, or the adhesive can be configured to partially or completely biodegrade within about 24 hours, 18 hours, 12 hours, 10 hours, 8 hours, 6 hours, or less;
(vi) the weight of the adhesive layer per surface area of the patch is in the range of about 7 g/m2 to about 100 g/m2 (e.g., 7-20 g/m2, 20-30 g/m2, 30-40 g/m2, 40-50 g/m2, 50-75 g/m2, 75-100 g/m2, and overlapping ranges thereof);
(vii) the adhesive layer has a surface area of between about 1 square inch and about 2 square inches;
(viii) the adhesive comprises an acrylic component, and does not comprise a silicone component;
(ix) the acrylic component comprises between about 50% and about 97% by weight of an acrylic polymer (e.g., 50-60%, 60-70%, 70-80%, 80-97%, and overlapping ranges thereof), and between about 3% and 50% (e.g., 3-20%, 20-30%, 30-40%, 40-50%, and overlapping ranges thereof) by weight of an acrylic acid.
(x) the acrylate is selected from the group consisting of: isooctyl acrylate, 2-ethyl hexyl acrylate, isononyl acrylate, decyl acrylate, dodecyl acrylate, butyl acrylate, hexyl acrylate, and mixtures thereof;
(xi) the adhesive comprises a hydrocolloid component;
(xii) the adhesive comprises an MVTR that can be greater than or equal to about 400 $g/m^2$, 500 $g/m^2$, 600 $g/m^2$, 700 $g/m^2$, 800 $g/m^2$, 900 $g/m^2$, 1000 $g/m^2$, 1100 $g/m^2$, 1200 $g/m^2$, 1300 $g/m^2$, 1400 $g/m^2$, 1500 $g/m^2$, 2000 $g/m^2$, 2500 $g/m^2$, 3000 $g/m^2$, 3500 $g/m^2$, 4000 $g/m^2$, 4500 $g/m^2$, 5000 $g/m^2$, or more per day, or be between about 3500 $g/m^2$ and 5000 $g/m^2$, between about 4000 $g/m^2$ and 4500 $g/m^2$, or about 4200 $g/m^2$ per day;
(xiii) the device can be between about 0.5 inches and about 3 inches long (e.g., 0.5-1 inches, 1-2 inches, 2-3 inches, and overlapping ranges thereof) at its longest, between about 0.5 inches and about 2 inches wide (e.g., 0.5-1 inches, 1-1.5 inches, 1.5-2 inches, and overlapping ranges thereof) at its widest, and/or have a thickness of between about 0.0001 inches and about 0.1 inches (e.g., 0.0001-0.001 inches, 0.001-0.01 inches, 0.01-0.1 inches, and overlapping ranges thereof) at its thickest point;
(xiv) the support structure when applied has a contact surface that is configured to directly contact and adhere to the skin of one or more clitoral structures selected from the group consisting of one or more of the following: the clitoral shaft, clitoral hood, and the clitoral glans;
(xv) the support structure when applied is configured to apply a mechanical force to the one or more clitoral structures sufficient to neuromodulate one or more clitoral nerves while not causing sexual arousal,
(xvi) the support structure further comprises one or more of the following features selected from the group consisting of: a contoured portion; a raised portion; a tab; and a malleable portion,
(xvii) the contoured portion, raised portion, and/or malleable portion are configured to facilitate maintenance of the mechanical force on the one or more clitoral structures while the patient is at rest and/or during activity;
(xviii) the contoured portion has a curvature of between about 10% and about 30% along an axis of the device;
(xix) the support structure comprises the raised portion;
(xx) the raised portion encompasses the center of the contact surface of the support structure;
(xxi) the contact surface comprises the raised portion having a surface area and a non-raised portion having a surface area, wherein the raised portion has a surface area that is between about 10% and about 100% of the surface area of the non-raised portion;
(xxii) the raised portion has a maximum thickness that is at least about 10% greater than the thickness of a non-raised portion of the device;
(xxiii) the tab does not comprise adhesive;
(xxiv) the malleable portion is sufficiently malleable to stably deform from a first configuration to a second configuration, the second configuration conforming to the shape of the one or more clitoral structures;
(xxv) the device comprises a backing layer coupled to the adhesive layer, the backing layer comprising a flexible film material;
(xxvi) the device comprises one or more depressions configured to apply a radial mechanical force to the clitoral structures;
(xxvii) the device comprises one or more stiffening members;
(xxviii) the stiffening members comprise a shape memory material;
(xxix) the stiffening members extend around at least a portion of the perimeter of the device.

EXAMPLE 5

In one embodiment, a subject identified as having a pelvic disorder (such as stress or urge urinary incontinence) will obtain a formulation, either alone or on a device (e.g., without professional intervention) for application to the pelvic area (e.g., one or more clitoral structures), wherein the formulation includes one or more (or all) of the following features;

(i) a biocompatible adhesive sufficient for topical application to a clitoral structure, wherein the adhesive does not comprise silicone;
(ii) the formulation is provided in an amount and on a device sufficient to apply mechanical pressure or traction to a clitoral structure such that one or more clitoral nerves will be neuromodulated to a sub-sexual arousal level;
(iii) the formulation may be configured such that when removed from the clitoral structures less than about 50%, 40%, 30%, 20%, 10%, or less of the adhesive surface area is covered by detached skin cells of the patient;

(iv) the formulation can be configured to decouple from the patient's clitoral structures within about 24 hours, 18 hours, 1:2 hours, 10 hours, 8 hours, 6 hours, or less;

(v) the formulation can be configured to partially or completely biodegrade within about 24 hours, 18 hours, 12 hours, 10 hours, 8 hours, 6 hours, or less;

(vi) the formulation comprises an acrylic component, and does not comprise a silicone component;

(vii) the acrylic component comprises between about 50% and about 97% by weight of an acrylic polymer (e.g., 50-60%, 60-70%, 70-80%, 80-97%, and overlapping ranges thereof), and between about 3% and 50% (e.g., 3-20%, 20-30%, 30-40%, 40-50%, and overlapping ranges thereof) by weight of an acrylic acid.

(viii) the acrylate is selected from the group consisting of: isooctyl acrylate, 2-ethyl hexyl acrylate, isononyl acrylate, decyl acrylate, dodecyl acrylate, butyl acrylate, hexyl acrylate, and mixtures thereof;

(ix) the formulation comprises a hydrocolloid component;

(x) the formulation comprises an MVTR, that can be greater than or equal to about 400 $g/m^2$, 500 $g/m^2$, 600 $g/m^2$, 700 $g/m^2$, 800 $g/m^2$, 900 $g/m^2$, 1000 $g/m^2$, 1100 $g/m^2$, 1200 $g/m^2$, 1300 $g/m^2$, 1400 $g/m^2$, 1500 $g/m^2$, 2000 $g/m^2$, 2500 $g/m^2$, 3000 $g/m^2$, 3500 $g/m^2$, 4000 $g/m^2$, 4500 $g/m^2$, 5000 $g/m^2$, or more per day, or be between about 3500 $g/m^2$ and 5000 $g/m^2$, between about 4000 $g/m^2$ and 4500 $g/m^2$, or about 4200 $g/m^2$ per day.

(xi) the formulation can be used to treat a variety of pelvic conditions, including one or more of female stress, urge, and/or mixed urinary incontinence, urinary frequency, urgency, overactive bladder, interstitial cystitis, pelvic pain, vulvodynia, or endometriosis, wherein the formulation is placed on a patch, and wherein the formulation is configured for facilitating adhesion and pressure to the clitoral region.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "placing a device on the clitoris of a patient" include "instructing the placing of a device on the clitoris of a patient." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A device for treating a pelvic condition of a female patient, comprising:
    a support structure comprising an adhesive layer sized and configured for application between opposing folds of the labia majora,
    wherein the support structure when applied has a contact surface that is configured to directly contact and adhere to a skin of one or more clitoral structures selected from the group consisting of one or more of the following: a clitoral shaft, a clitoral hood, and a clitoral glans,
    wherein the support structure when applied is configured to apply a mechanical force to the one or more clitoral structures sufficient to stimulate one or more clitoral nerves while not causing sexual arousal,
    wherein an adhesive layer comprises an adhesive configured such that when removed from the clitoral structures less than 20% of the adhesive surface area is covered by detached skin cells of the patient,
    wherein a weight of the adhesive layer per surface area of the support structure is in a range of 7 $g/m^2$ to 100 $g/m^2$,
    wherein the support structure is between 0.5 inches and 3 inches long at its longest, between 0.5 inches and 2 inches wide at its widest, and has a thickness of between 0.0001 inches and 0.1 inches at its thickest point; and
    wherein the support structure further comprises one or more of the following features selected from the group consisting of:
    (a) a contoured portion;
    (b) a raised portion; a
    (c) a tab; and
    (d) a malleable portion,
    wherein the contoured portion, raised portion, and/or malleable portion are configured to facilitate maintenance of the mechanical force on the one or more clitoral structures while the patient is at rest and/or during activity.

2. The device of claim 1, wherein the support structure comprises the raised portion.

3. The device of claim 2, wherein the raised portion encompasses a center of a contact surface of the support structure.

4. The device of claim 2, wherein a contact surface comprises the raised portion having a surface area and a non-raised portion having a surface area, wherein the raised portion has a surface area that is between 10% and 100% of the surface area of the non-raised portion.

5. The device of claim 2, wherein the raised portion has a maximum thickness that is at least 10% greater than the thickness of a non-raised portion of the device.

6. The device of claim 1, wherein the device comprises one or more stiffening members.

7. The device of claim 6, wherein the stiffening members comprise a shape memory material.

8. The device of claim 6, wherein the stiffening members extend around at least a portion of a perimeter of the device.

9. The device of claim 1, wherein the support structure comprises the contoured portion.

10. The device of claim 9, wherein the contoured portion has a curvature of between 10% and 30% along an axis of the device.

11. The device of claim 1, further comprising the tab.

12. The device of claim 11, wherein the tab does not comprise adhesive.

13. The device of claim 1, further comprising the malleable portion.

14. The device of claim 13, wherein the malleable portion is sufficiently malleable to stably deform from a first configuration to a second configuration, the second configuration conforming to a shape of the one or more clitoral structures.

15. The device of claim 1, wherein the device comprises a backing layer coupled to the adhesive layer, the backing layer comprising a flexible film material.

16. The device of claim 15, further comprising an absorbent material coupled to the backing layer.

17. A system comprising the device of claim 1, and a urethral plug.

18. The system of claim 17, wherein the device is coupled to the urethral plug.

19. The device of claim 1, wherein the adhesive is configured such that when removed from the clitoral structures less than 10% of the adhesive surface area is covered by detached skin cells of the patient.

20. The device of claim 1, wherein the device comprises one or more depressions configured to apply a radial mechanical force to the clitoral structures.

* * * * *